US011753616B2

(12) United States Patent
Birnboim et al.

(10) Patent No.: US 11,753,616 B2
(45) Date of Patent: Sep. 12, 2023

(54) COMPOSITION AND METHOD FOR STABILIZING AND MAINTAINING THE VIABILITY OF HARDY MICROORGANISMS

(71) Applicant: DNA Genotek Inc., Kanata (CA)

(72) Inventors: H. Chaim Birnboim, Ottawa (CA); Cassandra Kelly-Cirino, Kanata (CA); Bitapi Ray, Stittsville (CA); Jacques Oscar Everard Niles, Stittsville (CA); Olle Maarten de Bruin, Ottawa (CA)

(73) Assignee: DNA Genotek, Inc., Kanata (CA)

( * ) Notice: Subject to any disclaimer, the term of this patent is extended or adjusted under 35 U.S.C. 154(b) by 430 days.

(21) Appl. No.: 15/313,812

(22) PCT Filed: May 27, 2015

(86) PCT No.: PCT/CA2015/050480
§ 371 (c)(1),
(2) Date: Nov. 23, 2016

(87) PCT Pub. No.: WO2015/179976
PCT Pub. Date: Dec. 3, 2015

(65) Prior Publication Data
US 2017/0226469 A1 Aug. 10, 2017

Related U.S. Application Data

(60) Provisional application No. 62/003,114, filed on May 27, 2014.

(51) Int. Cl.
| | |
|---|---|
| *C12N 1/04* | (2006.01) |
| *C12N 1/20* | (2006.01) |
| *C12Q 1/24* | (2006.01) |
| *C12Q 1/00* | (2006.01) |

(52) U.S. Cl.
CPC .............. *C12N 1/20* (2013.01); *C12N 1/04* (2013.01); *C12Q 1/00* (2013.01); *C12Q 1/24* (2013.01)

(58) Field of Classification Search
None
See application file for complete search history.

(56) References Cited

U.S. PATENT DOCUMENTS

| 6,350,578 B1 * | 2/2002 | Stark | C12Q 1/6806 435/6.14 |
|---|---|---|---|
| 6,383,393 B1 * | 5/2002 | Colpan | C12N 15/101 210/198.2 |
| 6,979,449 B1 * | 12/2005 | Mock | A61K 39/07 424/193.1 |
| 8,158,357 B2 * | 4/2012 | Birnboim | C12Q 1/6806 435/6.1 |
| 2004/0043453 A1 * | 3/2004 | Drocourt | G01N 33/569 435/69.1 |
| 2004/0062785 A1 * | 4/2004 | Parker | A01N 25/006 424/410 |
| 2007/0111206 A1 * | 5/2007 | Tyagi | C12Q 1/689 435/6.14 |
| 2010/0099149 A1 * | 4/2010 | Birnboim | C12N 15/1003 435/91.3 |
| 2013/0209997 A1 * | 8/2013 | Whitney | C12Q 1/6806 435/6.1 |
| 2017/0130219 A1 | 5/2017 | Birnboim et al. | |

FOREIGN PATENT DOCUMENTS

| CN | 1856570 A | 11/2006 |
|---|---|---|
| CN | 1856570 A | 11/2006 |
| CN | 101153263 A | 4/2008 |
| CN | 101175853 A | 5/2008 |
| CN | 101253273 A | 8/2008 |
| EP | 0285439 | 10/1988 |
| JP | H09168399 | 6/1997 |
| JP | 2010505396 | 2/2010 |
| WO | WO 03/104251 A2 | 12/2003 |
| WO | WO2005/010186 | 2/2005 |
| WO | WO2006/096973 | 9/2006 |
| WO | WO2007/068094 | 6/2007 |
| WO | WO2008/040126 | 4/2008 |
| WO | 2012098854 A1 | 7/2012 |
| WO | WO2012/098254 | 7/2012 |
| WO | WO2015/154189 | 10/2015 |

OTHER PUBLICATIONS

Hervas-Aguila., JBC, 282(48):34735-34747 (2007) (Year: 2007).*
Setlow, J. App. Bacteriol. Symp. Suppl., 76:49S-60S (1994) (Year: 1994).*
Carricajo et al., J. Clin. Microbiol., 39(10):3799-3800 (2001) (Year: 2001).*
King et al., "Environmental reservoirs of pathogenic mycobacteria across the Ethiopian biogeographical landscape", PLOS ONE, vol. 12, e0173811, p. 1-15 (Year: 2017).*
Burdz et al., "Evaluation of sputum decontamination methods for *Mycobacterium tuberculosis* using viable colony counts and flow cytometry", Diagnostic Microbiology and Infectious Disease, vol. 47, p. 503-509 (Year: 2003).*
Padilla et al., "Comparison of the Sodium Hydroxide Specimen Processing Method with the C18-Carboxypropylbetaine Specimen Processing Method Using Independent Specimens with Auramine Smear, the MB/BacT Liquid Culture System, and the COBAS Test", Journal of Clinical Microbiology, vol. 43, p. 6091-6097 (Year: 2005).*
International Search Report and Written Opinion for International Application No. PCT/CA2015/050480 dated Aug. 21, 2015.
International Preliminary Report on Patentability for International Application No. PCT/CA2015/050480 dated Feb. 17, 2016.

(Continued)

*Primary Examiner* — Michelle F. Paguio Frising
(74) *Attorney, Agent, or Firm* — Cook Alex Ltd.

(57) ABSTRACT

The present application is to provide a composition and method for stabilizing and maintaining the viability of hardy microorganisms from sample collection to downstream analysis. In particular, there is a method for preserving viable hardy bacteria, such as *Mycobacteria, Bacillus anthracis*, or *Clostridium difficile*, in a biological sample, comprising contacting the biological sample with a stabilization composition, wherein the stabilization composition comprises a chelating agent, a denaturing, a salt and has a pH between about 6 and about 11.

17 Claims, 6 Drawing Sheets

(56) References Cited

OTHER PUBLICATIONS

Extended European Search Report dated Nov. 30, 2017 issued in respect of corresponding European Patent Application No. 15798676.1.
Communication pursuant to Article 94(3) EPC dated Mar. 3, 2019 issued in respect of corresponding European Patent Application No. 15798676.1.
K. Kassaza et al. "Lowenstein-Jensen Selective Medium for Reducing Contamination in Mycobacterium tuberculosis Culture", Journal of Clinical Microbiology, vol. 52, No. 7, Apr. 30, 2014, pp. 2671-2673.
First Office Action dated Feb. 3, 2019 issued in respect of corresponding Chinese Appln. No. 2015800277515.
First Office Action dated Mar. 15, 2018 issued in respect of corresponding Eurasian Patent Application No. 201692258.
Second Office Action dated Oct. 12, 2018 issued in respect of corresponding Eurasian Patent Application No. 201692258.
Third Office Action dated May 23, 2019 issued in respect of corresponding Eurasian Patent Application No. 201692258.
Notice of Reasons for Rejection dated Apr. 2, 2019 issued in respect of corresponding Japanese Patent Application No. 2016-569691.
Office Action dated Apr. 2, 2019 issued in respect of corresponding Indonesian Patent Application No. P00201608958.
Burdz TV, Wolfe J, Kabani A (2003) Evaluation of sputum decontamination methods for Mycobacterium tuberculosis using viable colony counts and flow cytometry. Diagn Microbiol Infect Dis 47: 503-509.
Dorman SC, Bussoli MA, Ritz SA (2010) Alcohol fixation of induced sputum samples for applications in rural communities. Can Respir J 17(3): 115-121.
Effthimiadis A, Jayaram L, Weston S, Carruthers, S, Hargreave FE (2002) Induced sputum: Time from expectoration to processing. Eur Respir J 19: 706-708.
Gopinath K and Singh S (2009) Multiplex PCR assay for simultaneous detection and differentiation of Mycobacterium tuberculosis, Mycobacterium avium complexes and other Mycobacterial species directly from clinical specimens. J Appl Microbiol 107: 425-435.
Halse TA, Edwards J, Cunningham PL, Wolfgang WJ, Dumas NB, Escuyer VE, Musser KA (2010) Combined real-time PCR and rpoB gene pyrosequencing for rapid identification of Mycobacterium tuberculosis and determination of rifampin resistance directly in clinical specimens. J Clin Microbiol 48(4): 1182-1188.
Hammerschlag MR, Harding L, Macone A, Smith AL, Godlmann DA (1980) Bacteriology of sputum in cystic fibrosis: Evaluation of dithiothreitol as a mucolytic agent. J Clin Microbiol 11(6): 552-557.
Holz O, Mücke M, Zarza P, Loppow D, Jörres RA, Magnussen H (2001) Freezing of homogenized sputum samples for intermittent storage. Clin Exp Allergy 31: 1328-1331.
Kelly MM, Hargreave FE, Cox GE (2003) A method to preserve sputum for delayed examination. Eur Respir J 22: 996-1000.
Lipsky BA, Gates J, Tenover FC, Plorde JJ (1984) Factors affecting clinical value of microscopy for acid-fast bacilli. Rev Infect Dis 6: 214-222.
US Centers for Disease Control and Prevention (CDC, 2009) Updated guidelines for the use of nucleic acid amplification tests in the diagnosis of tuberculosis. MMWR Morb Mortal Wkly Rep 58: 7-10.
Morris S, Bai GH, Suffys P, Portillo-Gomez L, Fairchok M, Rouse D (1995) Molecular mechanisms of multidrug resistance in clinical isolates of Mycobacterium tuberculosis. J Infect Dis 171: 954-960.
Park H, Jang H, Kim C, Chung B, Chang CL, Park SK, Song S (2000) Detection and identification of mycobacteria by amplification of the internal transcribed spacer regions with genus and species-specific PCR primers. J Clin Microbiol 38: 4080-4085.
Parmasivan CN, Narayana AS, Prabhakar R, Rajagopal MS, Somasundaram PR, Tripathy SP (1983) Effect of storage of sputum specimens at room temperature on smear and culture results. Tubercle 64(2): 119-124.
Popov TA, Petlichkovski A, Mustakov TB, DuBushe LM, Popova DN (2004) Assessment of a protocol for sputum freezing and subsequent examination. J Allergy Clin Immunol 113: S193.
Selvam JM, Wares F, Perumal M, Gopi PG, Sudha G, Chandrasekaran V, Santha T (2007) Health-seeking behaviour of new smear-positive TB patients under a DOTS programme in Tamil Nadu, India. Int J Tuberc Lung Dis 11: 161-167.
Telenti A, Marchesi F, Balz M, Bally F, Bottger EC, Bodmer T (1993) Rapid identification of mycobacteria to the species level by polymerase chain reaction and enzyme analysis. J Clin Microbiol 31: 175-178.
Thornton CG, MacLellan KM, Brink TL JR, Lockwood DE, Romagnoli M, Turner J, Merz WG, Schwalbe RS, Moody M, Lue Y, Passen S (1998) Novel method for processing respiratory specimens for detection of mycobacteria by using C18-carboxypropylbetaine: Blinded study. J Clin Microbiol 36(7): 1996-2003.
Wilson ML (1996) General principles of specimen collection and transport. Clin Inf Dis 22: 766-777.
Global tuberculosis report 2013, WHO.
WHO. 2001. Global tuberculosis control. WHO/CDS/TB/2001 287:18-19.
PT Kent and GP Kubica (1985) Public Health Microbiology, a Guide for the Level III Laboratory, Centers for Disease Control, Division of Laboratory Training and Consultation. Atlanta, GA, US Department of Health and Human Services, US Government Printing Office.
Haise T. A. et al. (Jul. 2011) Evaluation of a Single-Tube Multiplex Real-Time PCR for Differentiation of Members of the Mycobacterium tuberculosis Complex in Clinical Specimens. Journal of Clinical Microbiology, vol. 49, No. 7, p. 2562-2567.
Krasnow I, Wayne LG (1966) Sputum digestion. I The mortality rate of tubercle bacilli in various digestion systems. Am J Clin Pathol 45: 352-355.
Silverstolpe L (1948) Förbättrad meted för påvisande av tuberkelbakterier. Nord Med 48: 2220-2222.
Communication pursuant to Article 94(3) EPC dated Oct. 21, 2019 issued in respect of corresponding European Patent Application No. 15798676.1 (8 pages).
Second Office Action dated Aug. 19, 2019 issued in respect of corresponding Chinese Appln. No. 2015800277515 (13 pages).
Office Action dated Apr. 2, 2020 issued in respect of corresponding Indonesian Patent Application No. P00201608958, with English translation (5 pages).
Notice of Reasons for Rejection dated Jan. 7, 2019 issued in respect of corresponding Japanese Patent Application No. 2016-569691,with English translation (8 pages).
Decision of Refusal dated Jul. 28, 2020 issued in respect of corresponding Japanese Patent Application No. 2016-569691, with English translation (2 pages).
Examination Report dated Jan. 11, 2021 issued in respect of corresponding European Patent Application No. 15798676.1.
Office Action issued in connection with patent application No. 2,950,419 by the Canadian Intellectual Property Office dated Sep. 9, 2021.

* cited by examiner

FIG. 5

COMPOSITION AND METHOD FOR STABILIZING AND MAINTAINING THE VIABILITY OF HARDY MICROORGANISMS

CROSS-REFERENCE TO RELATED APPLICATIONS

The present application is a U.S. National Stage of International Patent Application No. PCT/CA2015/050480, filed May 27, 2015, which claims the benefit of U.S. Provisional Application No. 62/003,114, filed May 27, 2014, both of which are incorporated herein by reference in their entireties.

FIELD OF THE INVENTION

The present application pertains to the field of sample collection and storage. More particularly, the present application relates to compositions and methods for maintaining the viability of hardy microorganisms from sample collection to analysis.

INTRODUCTION

Tuberculosis (TB) remains a major global health problem. The majority of new infections and deaths occur in developing countries. In 2012 alone, the World Health Organization (WHO) estimated 8.6 million people developed TB and 1.3 million died from the disease, including 320,000 deaths among HIV-positive individuals (Global tuberculosis report 2013, WHO). The number of TB deaths is unacceptably large given that most are preventable. The WHO estimates that approximately one-third of the world's population or 2 billion people are infected with tuberculosis and hence at risk of developing active disease. Alarmingly, the WHO estimated that only one-third of the 3.6 million smear-positive cases of TB were reported in 2001 (WHO. 2001. Global tuberculosis control. WHO/CDS/TB/2001 287:18-19). Early diagnosis of TB remains one of the primary hurdles in curtailing the spread of this disease. Unfortunately, there are a myriad of problems associated with identifying the approximately 30 million individuals worldwide with active TB.

Proper handling of biological specimens from the time of collection through all stages of transport, storage, and processing is crucial for obtaining microbiological test results that are both timely and clinically relevant (Wilson, 1996). Issues common to all clinical specimens submitted for microbiological testing include not only proper identification, but also collection techniques that maximize recovery of microbial pathogens and minimize contamination by non-pathogens. For specimens such as sputum, feces and urine, the relative proportions of microorganisms present in vivo must be preserved, or culture results may be misleading. If specimens are handled properly, culture results are easier to interpret, patient care is improved, and costs are potentially decreased.

Recently, an emphasis has been placed on guidelines for specimen handling to modify traditional practices to decrease or eliminate unnecessary work, increase laboratory efficiency, and make microbiological testing more cost-effective. It has been a long standing goal of medical science to develop rapid and accurate procedures for the diagnosis of infectious disease to improve case finding, to reduce time for diagnosis and initiation of treatment, to improve disease surveillance, and have fewer patients dropping out of the diagnostic pathway. The laboratory diagnosis of enteric infections is particularly challenging. Problems include the number of potential pathogens, the biological diversity of these organisms, the emergence of new pathogens, intermittent shedding of some pathogens, multiple specimens are submitted from the same patient, impracticality of testing of fresh specimens in most clinical settings (particularly in outpatient and remote settings), and the cost of transport of specimens to laboratories for culture and molecular diagnostic testing.

Expectorated sputum is the most commonly collected respiratory specimen for bacterial cultures to detect the most frequent causative agent of TB, *Mycobacterium tuberculosis* (MTB). Because respiratory tract specimens will contain "contaminating" microorganisms, specimens should be collected and transported promptly to the laboratory to avoid overgrowth of non-pathogens. Traditionally, the delay between collection and culture inoculation should not exceed 7 days and specimens should be refrigerated until they can be processed. Prompt transport, processing and refrigeration help prevent the death of mycobacteria and the overgrowth of normal fast-growing flora in specimens, which otherwise complicate the recovery and detection of pathogens. Processing overgrown or putrefied specimens, if feasible, entails additional labour costs and reductions in culture sensitivity when sputum is stored at room temperature for longer than 3 days (Parmasivan et al., 1983). Unless specimens are collected with utmost care and promptly transported to the laboratory under proper conditions, the advantages of culture will not be fully realized.

Proper sputum collection is critical for optimal results. Ideally, from a new patient, three specimens (2-10 mL each) should be collected in the early morning on consecutive days and should be processed separately. The WHO recommends two early morning specimens and a third spot specimen when a patient visits the clinic. A reduction from three to two in the number of specimens to be examined for screening TB cases has already been accepted in places with high workloads and limited human resources, provided that quality assurance programmes are implemented.

Once received in the laboratory, these highly mucoid specimens must be liquefied and "decontaminated" prior to smear microscopy and culture. The standard procedure recommended by the Centers for Disease Control and Prevention (CDC) is the N-acetyl-L-cysteine (NALC)-sodium hydroxide (NaOH) procedure (PT Kent and GP Kubica; Public Health Microbiology, a Guide for the Level III Laboratory, CDC, Division of Laboratory Training and Consultation, 1985). NALC liquefies the mucoid specimen, while NaOH is bactericidal for contaminating/background bacteria and helps in liquefaction. NaOH also kills mycobacteria, but to a much lesser extent. A "smear-positive" case is defined in patients with at least two initial sputum smear examinations (direct smear microscopy) positive for acid-fast bacilli (AFB+).

A definitive diagnosis of active tuberculosis rests upon the recovery and subsequent identification of the causative organism from a patient's secretions, body fluids, or tissues. Since current culture methods require extended periods of time for completion (up to 42 days), initial management of the patient often is based upon the results of microscopic examination of the submitted clinical specimens. Specifically, demonstration of acid-fast bacilli (AFB) in a smear made from a clinical sputum specimen provides a preliminary diagnosis of mycobacterial disease, while the isolation of mycobacteria on culture provides a definite diagnosis of tuberculosis or similar disease due to mycobacteria other than *M. tuberculosis* (MOTT bacilli) or non-tuberculosis mycobacteria (NMT). While smear microscopy is currently the most widely used screening tool, considerable controversy exists regarding the predictive value of this procedure. It is estimated that microscopy can miss two-thirds of culture-positive cases (Lipsky et al., 1984). As a consequence, culture techniques still play a key role in the diagnosis of mycobacterial disease.

The nature of both sputum specimens and the standard processing method (NALC/NaOH) compromises the detection of MTB (Thornton et al., 1998). First, the specimens, as well as the solutions used to process specimens, can inhibit nucleic acid amplification. Most specimens contain large numbers of saprophytic and/or infectious microorganisms that interfere with culture methods; hence, a decontamination step is essential. However, decontamination is known to significantly compromise the viability of mycobacteria (Burdz et al., 2003; Krasnow and Wayne, 1966), and thus processing lowers the sensitivity of detection by culture as well. Second, the innate nature of the disease produces low copy number and only intermittent shedding of the organisms. The third problem relates to the inherent physiological nature of the mycobacteria itself which includes i) aggregation, clumping, and cording; ii) surface tension caused by the waxy cell wall; iii) buoyancy (which ranges from 0.79 to 1.07, with an average below 1) (Silverstolpe, 1948); (iv) slow growth; and iv) a thick cell wall making *Mycobacterium tuberculosis* difficult to lyse. Together with the mucoid nature of sputum, these properties complicate the collection of mycobacteria by centrifugation causing inefficient sedimentation of these bacilli. Inevitably, some bacilli are poured off with the supernatant fraction following centrifugation. All methods approved by the CDC for preparing clinical specimens for detection involve a centrifugation step. The net effect is that mycobacteria are so scarce in processed sediments that some aliquots have no target bacilli and the few microorganisms that are collected must be efficiently lysed or must be viable to compete with contaminating bacteria. Finally, the low copy number of MTB requires large specimen volumes, which in turn demands the concentration-decontamination step.

Several groups have tried to develop a method to preserve sputum specimens, so samples can be collected in remote areas and sent to larger centers for processing. Holz et al. (2001) and Popov et al (2004) demonstrated that samples can be successfully frozen for up to 10 days before processing. However, shipping frozen samples is costly and the method may not be feasible in remote and rural areas if liquid nitrogen is not available. Kelly et al. (2003) tested a more cost-effective method of shipping samples, i.e., fixation in formaldehyde before processing. However, this method requires significant changes in sample processing methodology, increases the cost of processing, and MTB organisms are no longer viable for the historical "gold" standard test, culture. Similarly, Dorman et al. (2010) used alcohol (50% (by volume) ethyl alcohol) to preserve induced sputum samples; again making MTB no longer viable for culture.

There remains a need for a collection method and compositions that can liquefy sputum and retain the viability of MTB and other hardy microorganisms, while killing the background flora.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide a composition and method for stabilizing and maintaining the viability of hardy microorganisms. In accordance with an aspect of the present application, there is provided a method for preserving viable hardy bacteria, such as *Mycobacteria, Bacillus anthracis, Clostridium difficile* or yeast, in a biological sample, comprising contacting the biological sample with a stabilization composition, wherein the stabilization composition comprises a chelating agent, a denaturing agent, a salt and has a pH between about 6 and about 11.

In accordance with another aspect of the application, there is provided a method for liquefying a biological sample comprising contacting the biological sample with a stabilization composition, where in the stabilization composition comprises a chelating agent, a detergent, a salt and has a pH between 6 and 11.

In accordance with another aspect of the application, there is provided a method for stabilizing the microbiome within a biological sample comprising contacting the biological sample with a stabilization composition, where in the stabilization composition comprises a chelating agent, a detergent, a salt and has a pH between 6 and 11.

In accordance with another aspect of the application, there is provided a method for characterization of bacterial nucleic acid in a biological sample, comprising:

contacting the biological sample with a stabilization composition, where in the stabilization composition comprises a chelating agent, a detergent, a salt and has a pH between 6 and 11; and amplifying the nucleic acid in the sample, wherein the level of amplified nucleic acid remains substantially unchanged if the amplification step occurs immediately after collection, or later.

In accordance with another aspect of the application, there is provided a composition comprising: a chelating agent; a detergent; and viable hardy microorganisms.

BRIEF DESCRIPTION OF THE FIGURES

For a better understanding of the present invention, as well as other aspects and further features thereof, reference is made to the following description which is to be used in conjunction with the accompanying drawings, where:

FIG. 5 graphically depicts the viability of *B. anthracis* spores following treatment with Sample Transport Chemistry (STC).

DETAILED DESCRIPTION

Figure 1:
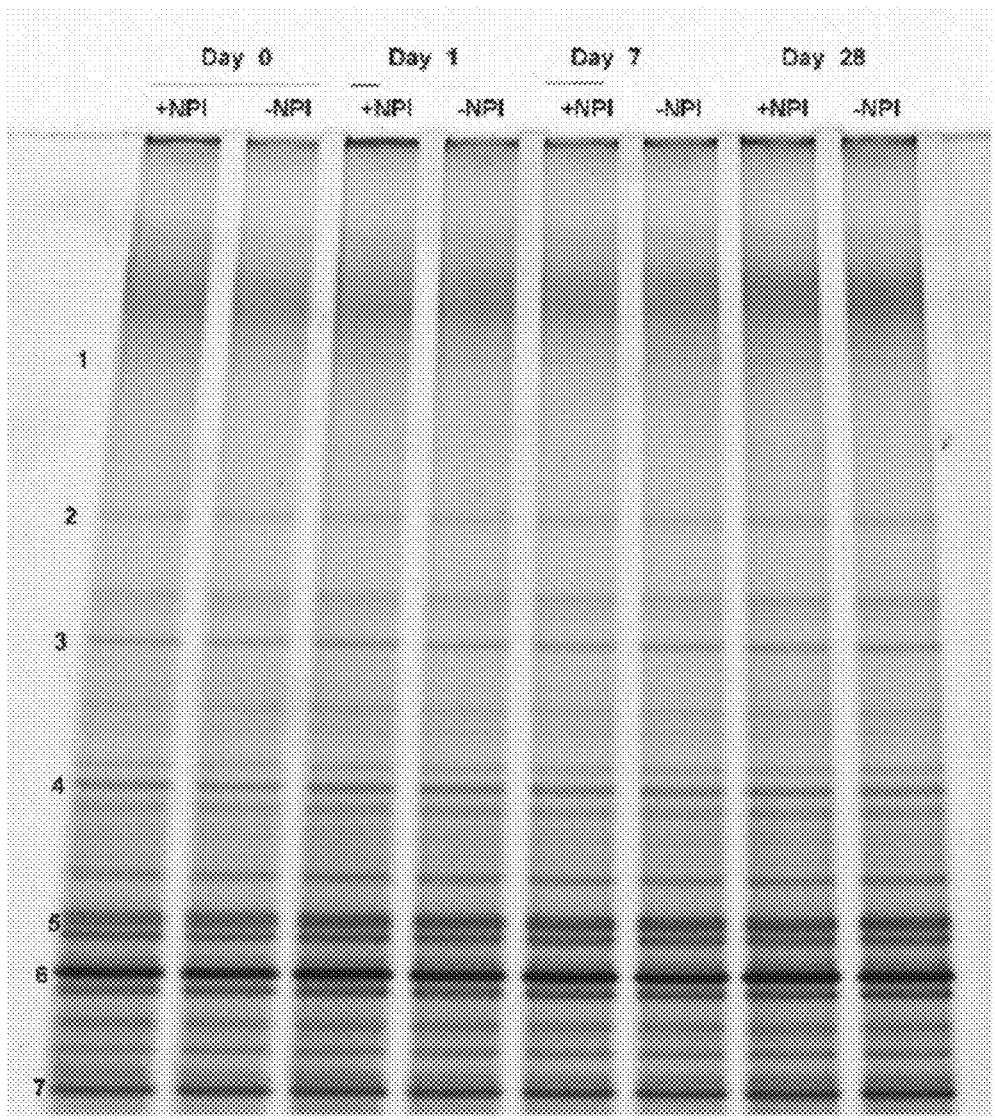
FIG. 1 is a photograph of the gel from Denaturing Gradient Gel Electrophoresis (DGGE) analysis of sputum stored at room temperature in BD2 buffer.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising," as used herein will be understood to mean that the list following is non-exhaustive and may or may not include any other additional suitable items, for example one or more further feature(s), component(s) and/or ingredient(s) as appropriate.

The term "sample" as used herein will be understood to mean any specimen that potentially contains a substance of interest, which is optionally a nucleic acid, protein or other biomolecule of interest. The term "sample" can encompass a solution, such as an aqueous solution, cell, tissue, biopsy, powder, solid, or population of one or more of the same. The sample can be a biological sample, such as saliva, sputum, buccal swab sample, serum, plasma, blood, buffy coat, pharyngeal, nasal/nasal pharyngeal or sinus swabs or secretions, throat swabs or scrapings, urine, mucous, feces, rectal swabs, lesion swabs, chyme, vomit, gastric juices, pancreatic juices, gastrointestinal juices, semen/sperm, urethral swabs and secretions, cerebral spinal fluid, products of lactation or menstruation, egg yolk, amniotic fluid, aqueous humour, vitreous humour, cervical secretions or swabs, vaginal fluid/secretions/swabs or scrapings, bone marrow samples and aspirates, pleural fluid and effusions, sweat, pus, tears, lymph, bronchial or lung lavage or aspirates, peritoneal effusions, cell cultures and cell suspensions, connective tissue, epithelium, epithelial swabs and smears, mucosal membrane, muscle tissue, placental tissue, biopsies, exudates, organ tissue, nerve tissue, hair, skin, nails, plants, plant extracts, algae, soil samples, environmental sample, sewage, wastewater, foodstuff, meat-processing equipment swabs or the like.

The term "microorganism" as used herein, will be understood to mean any microscopic organisms and spores, including all of the prokaryotes, namely the eubacteria and archaeabacteria, and various forms of eukaryote, comprising the protozoa, fungi (e.g., yeast), algae, and animals such as rotifers and planarians.

The term "hardy microorganism," as used herein, refers to microorganisms and spores that are generally resistant to standard lysis or nucleic extraction techniques, such as, one or more species of the *Mycobacterium* genus, one or more species of the *M. tuberculosis* complex, MDR strains of *M. tuberculosis*, one or more species of *Clostridium*, one or more species of *Bacillus*, such as *Bacillus anthracis*, and other microorganisms with hardy cell walls The terms "Sample Transport Chemistry composition" and "STC composition," as used herein, refer to compositions that are used to treat and/or store biological samples in order to maintain viability of hardy microorganisms that may or may not be present in the biological samples.

The present application provides a composition and method for stabilizing hardy microorganisms in biological samples. The present composition and method is also useful for liquefying viscous biological samples and/or for eliminating or minimizing growth of background bacterial flora in the biological samples during ambient temperature storage.

Sample Transport Chemistry

The present stabilization compositions comprise a sample transport chemistry ("STC") mixture that has been found to function successfully in stabilizing hardy microorganisms, such as *Mycobacteria*, in stored samples such that the hardy microorganisms remain viable for downstream clinical testing. In particular, the hardy microorganisms stored in the STC compositions are viable for culture under standard culture conditions even following storage at room temperature. The hardy microorganisms have been found to remain viable for later culture after storage at room temperature in an STC composition for 1 day or more, for 5 days or more, for a week or more. In one embodiment, the STC composition is useful for storing viable hardy microorganisms in a biological sample at room temperature for about a week. In this context, the hardy bacteria is understood to be "stabilized" if it remains viable for bacterial culture, as determined by the formation of colony forming units of the hardy bacteria under standard culture conditions.

The STC compositions of the present application are aqueous compositions that comprise a chelating agent, a denaturing agent and a salt and have a pH between about 6 and about 11. Alternatively, the STC compositions of the present application comprise a chelating agent, a denaturing agent, a salt and, optionally, a buffering agent that can be reconstituted by mixture with water, an aqueous solution, or a sample such that the pH of the final mixture is between about 6 and about 11.

The chelating agent is any chemical that will form a stable complex with certain metal ions, sequestering the ions so that they cannot normally react with other components. A chelator can be, for example, ethylene glycol tetraacetic acid (EGTA), (2-hydroxyethyl)ethylenediaminetriacetic acid (HEDTA), diethylene triamine pentaacetic acid (DTPA), nitrilotriacetic acid (NTA), ethylenediaminetriacetic acid (EDTA), cyclohexanediaminetetraacetic acid (CDTA), N,N-bis(carboxymethyl)glycine, citrate anhydrous, sodium citrate, calcium citrate, ammonium citrate, ammonium bicitrate, citric acid, diammonium citrate, ferric ammonium citrate, lithium citrate, or any combination thereof. In one embodiment, the chelating agent is CDTA.

The denaturing agent is any chemical that can cause proteins to lose their native secondary and/or tertiary structures. A denaturing agent can be, for example, an anionic detergent, (such as, for example, sodium dodecyl sulfate (SDS), lithium dodecyl sulphate, sodium lauroyl sarcosinate (SLS), sodium laureth sulphate (SLES)), a cationic detergent (such as, for example, cetyltrimethyl ammonium bromide (CTAB), which may be used in certain embodiments) or a nonionic detergent (such as, for example, Tween, Triton X, or Brij). In one embodiment, the denaturing agent is SDS.

In one embodiment, the STC composition comprises 2% SDS, 12.5 mM CDTA, 250 mM LiCl, 50 mM glycine and has pH 10.5. In an alternative embodiment, the STC buffer comprises 4% SDS, 50 mM CDTA, 250 mM LiCl, 140 mM LiOH and has pH 6.8.

The STC composition additionally comprises a salt, which is preferably an inorganic salt. In one example, the salt is LiCl. In another example, the salt can be, for example, lithium bromide, lithium iodide, lithium acetate, or any combination thereof. In yet another example, the salt can be, for example, sodium borate, sodium bromide, sodium iodide, sodium iodate, sodium chloride, sodium fluoride, sodium acetate, sodium phosphate, sodium sulphate, or any combination thereof.

The STC composition has a neutral or basic pH. In certain embodiments, the pH is in the range of from 6 to 11, for example, the pH of the STC composition can be about 6.8, or about 10.5. In order to maintain the pH, the composition can further comprise a buffering agent, such as glycine. Alternatively, the composition is adjusted to the appropriate pH using acid or base, such as LiOH.

In one embodiment, the STC composition comprises 2% SDS, 12.5 mM CDTA, 250 mM LiCl, 50 mM glycine and has pH 10.5. In an alternative embodiment, the STC buffer comprises 4% SDS, 50 mM CDTA, 250 mM LiCl, 140 mM LiOH and has pH 6.8.

The present application further provides compositions comprising the STC composition components, as defined above, and viable hardy bacteria from a sample, such as a biological sample. In certain embodiments, the hardy bacteria is a *Mycobacteria*, such as *M. tuberculosis, Bacillus anthracis*, optionally in the form of spores, or *Clostridium difficile*.

Transport and Storage Methods

The present application further provides methods for storage of samples, such as biological samples. The method is particularly useful for storage of biological samples such that they are stabilized in a form suitable for use in downstream clinical diagnostic tests. The downstream clinical diagnostic tests can be, for example, in vitro culture or molecular diagnostics, such as PCR-based diagnostics or sequencing. However, other diagnostic tests can be employed on samples stabilized using the present STC composition.

The present storage method comprises the step of mixing or contacting a biological sample with an amount of the STC composition. The resulting mixture can be stored at room temperature or ambient temperature or at a temperature within the range of from about 4° C. to about 40° C. The amount of STC mixed with the sample can be varied to accommodate the needs of the user. For example, it can be varied based on the sample type and/or volume, the requirements of downstream analysis, convenience, etc. In one embodiment, the ratio of sample volume to STC composition volume ranges from about 5:1 to about 1:5. In a specific embodiment, the sample is mixed with an equal volume of the STC composition.

Preferably, the storage method is performed at the time of sample collection to avoid the need for later treatment of the sample before analysis. In this way, the potential for contamination and/or the need for specialized sample processing facilities are minimized. This can be achieved, for example, by providing the STC composition in a sample collection device.

The present inventors have determined that the present storage method is useful in stabilizing the microbiome of a sample. Specifically, the STC composition functions to inhibit growth of the microorganisms in the sample, while retaining the hardy bacteria in the sample viable for future culture. In this way, researchers or clinicians are able to analyze a sample well after sample collection and determine the microbial components and relative amounts of the microorganisms within a sample stored using the STC composition.

Accordingly, the present application further provides a method for stabilizing the microbiome of a sample, comprising the step of mixing or contacting the sample with an amount of the STC composition, as defined above.

Following treatment of a biological sample with the STC composition, the sample can be transported, stored, or analyzed using standard techniques as required by the user. In one embodiment, the microbiological nucleic acid in the sample is recovered or isolated from the sample. This can be done using standard techniques, or it can be done using a composition comprising an oxidizing agent and buffer, wherein the oxidizing agent is periodic acid, periodate or persulfate (as described in U.S. Provisional application No. 61/977,953, which is incorporated herein by reference).

Liquefaction of Highly Viscous Samples

The present application further provides a method for liquefying viscous, mucoid biological samples. Many biological, or bodily, samples are viscous. This can present significant challenges to accurate diagnostic testing since the samples are difficult to process and since the analytes, bacteria, etc, may not be uniformly dispersed in such viscous samples. Accordingly, it is particularly beneficial to have a method for sample processing that can reduce the viscosity of the sample and improve the uniformity of distribution of the sample components within the sample.

Diagnostic procedures often require the analysis of biological samples such as body fluids. In particular, nucleic acid based diagnostic methods are becoming more and more important. However, such methods generally require initial processing of the biological sample which may be time-consuming, laborious, and associated with the risk of contamination. For example, the diagnosis of tuberculosis involves the analysis of highly viscous liquid biological samples such as sputum, pus, pleural fluid, gastric aspirate, endotracheal aspirate, transtracheal aspirate, bronchoalveolar lavage, laryngeal swab, and nasopharyngeal swabs, which are usually inhomogeneous mixtures of many different components of different chemical and physical behavior. This can present significant challenges to accurate diagnostic testing since the samples are difficult to process and since the analytes, bacteria, etc, may not be uniformly dispersed in such samples. It would be beneficial to have a method for sample collection that can reduce the viscosity of the sample and improve the uniformity of distribution of the sample components within the sample.

Sputum consists of variable amounts of glycoproteins (mucins), saliva, immune cells, host tissue particles, released DNA, lipids, and proteins from lysed host tissue. Biochemical analyses have revealed that mucins MUC5AC and MUC5B secreted by cells lining the respiratory tract are the major gel-forming polymer components of airway mucus. Cysteine domains present on these mucins contribute to polymer formation and possibly interaction with neighboring mucin chains by disulfide bonding. Certain sputa can contain variable amounts of blood or residual food particles as contaminants. This results in a very extensive sample-to-sample variability of sputum composition ranging from homogeneous to multi-phasic on the one side and liquid to highly viscous on the other side. Dependent of the disease state of individual patients, sputa can furthermore contain inflammatory pathogens, and certain sample components can be extremely pronounced, e.g., blood contamination due to lung inflammation or elevated viscosity due to an extensive DNA release for cystic fibrosis or bronchitis patients.

Because of the extensive sample heterogeneity processing of sputum samples such as DNA isolation from sputum for diagnostic purposes is rather challenging. For instance, accessibility and lysis of inflammatory pathogens can be less efficient if they are trapped in a solid and viscous environment.

As noted herein, analysis of sputum samples is a standard diagnostic procedure for patients with suspected tuberculosis. The classical methods for diagnosis include examination of sputum smear under a microscope for acid-fast mycobacteria and microbiological analysis of cultured mycobacteria isolated from sputum, which is the current gold standard for identification of pathogens and resistances in tuberculosis diagnosis. In addition, some molecular tests have been developed. Generally, all these diagnostic methods aiming at detection of mycobacteria in sputum samples require laborious sample processing for decontamination and liquefaction using enzymes such as proteases, lipases, DNases, or glycosidases, detergents, chaotropic agents, chelating agents, and reducing agents among others. Due to the high infection risk any treatment of tuberculosis suspected sputa requires an S3 environment with certified laminar flows and extensive protection measures to exclude any exposure of personnel to live bacteria. Thus, for molecular tests it would be of advantage to use sputum directly for nucleic acid diagnostics and circumvent the handling intensive decontamination and liquefaction procedures.

The present inventors have surprisingly found that the STC composition functions to liquefy mucoid biological samples at much lower pH than used in NALC/NaOH, thereby improving the accuracy and/or ease of diagnostic testing, and enabling withdrawal of multiple uniform samples for a multitude of diagnostic tests (e.g. smear microscopy, culture, and molecular diagnostics).

In one aspect, there is provided a method of liquefying a sample, such as a biological sample, comprising the step of mixing or contacting the sample with an amount of the STC composition. The resulting mixture can be stored at ambient temperature, or less. The amount of STC mixed with the sample can be varied to accommodate the needs of the user. For example, it can be varied based on the sample type and/or volume, the requirements of downstream analysis, convenience, etc. In one embodiment, the ratio of sample volume to STC composition volume ranges from about 5:1 to about 1:5. In a specific embodiment, the sample is mixed with an equal volume of the STC composition.

Preferably, the method of liquefying the sample is performed at the time of sample collection to avoid the need for later treatment of the sample before analysis. In this way, the potential for contamination and/or the need for specialized sample processing facilities are minimized. This can be achieved, for example, by providing the STC composition in a sample collection device.

Method for Nucleic Acid Detection

As noted above, molecular diagnostic methods are becoming more important in the arsenal of tools used by researchers and clinicians in analyzing patient samples to identify the presence or absence of potential pathogens. These molecular methods can additionally be useful in quantifying the degree of infection when a pathogenic organism is present. While, molecular diagnostic methods are generally quite sensitive, samples having low levels of pathogen present can be difficult to accurately process to identify or quantify the pathogen present, particularly when the pathogen is a hardy bacteria and/or the nucleic acid from the pathogen is not efficiently released or isolated from the sample.

The present inventors have surprisingly found that the STC composition functions to efficiently release nucleic acid. The inventors have shown that samples treated with the STC composition had DNA available in sufficient quantities to be tested for antibiotic resistance markers on Day 0 of testing. In contrast, the standard of care method required the samples to be cultured to generate sufficient bacteria to generate a positive result.

Accordingly, the present application provides a method for characterization of bacterial nucleic acid in a biological sample, comprising contacting the biological sample with a stabilization composition, where in the stabilization composition comprises a chelating agent, a detergent, a salt and has a pH between 6 and 11; and amplifying the nucleic acid in the sample, wherein the level of amplified nucleic acid remains substantially unchanged if the amplification step occurs immediately after collection, or later, and wherein the sample does not require culture prior to amplifying the nucleic acid.

Kit

Methods of the invention are conveniently practiced by providing the STC compositions used in such method in the form of a kit. Such a kit preferably contains the STC composition as a mixture of dry components or as an aqueous mixture.

Optionally the kit includes a container, which contains the STC composition of the present invention and that is suitable for sample collection. Examples of suitable containers are those, described in International PCT Application Nos. WO 03/104251 and WO 07/068094, each of which is incorporated herein by reference.

To gain a better understanding of the invention described herein, the following examples are set forth. It should be understood that these examples are for illustrative purposes only. Therefore, they should not limit the scope of this invention in any way.

EXAMPLES

Example 1: Ambient Temperature Stability of *Mycobacterium tuberculosis*-Spiked Sputum Stored in Sample Transport Chemistry One of the major goals for the global control of TB in humans is the laboratory diagnosis of *M. tuberculosis*, the causative agent of TB, followed by adequate treatment. Difficulties involved in the collection, transport, and processing of sputum specimens have been a major issue in current global TB control efforts. *M. tuberculosis* is present in sputum specimens which are often contaminated by other fast growing microflora. The rapid growth of certain less clinically relevant species at ambient temperature can kill or overgrow medically important pathogens. Therefore, delays in either transport of specimens to the laboratory or availability of trained personnel or infrastructure to perform the processing are problematic.

In high-burden countries, sputum acid-fast bacilli (AFB) microscopy services are not available in many healthcare facilities, which can force a substantial proportion of pulmonary TB patients to travel long distances to avail diagnostic facilities (Selvam et al., 2007). This lack of infrastructure results in the loss of many patients during treatment and means that infectious patients transmit infection within and outside their community. In order to prevent this, India's DOTS-based Revised National Tuberculosis Control Programme (RNTCP), for instance, has recommended transportation of sputum specimens to microscopy centers. However, organization of such services is difficult for several reasons, including the fact that it necessitates transportation of highly contagious sputum samples. Further, transfer of specimens to one centralized laboratory facility can be somewhat erratic and possibly affect microbiologic yield and integrity.

Rapid loss of specimen integrity also presents a significant impediment to both international infectious disease research collaboration, as well as the study of pathogens in remote areas. It is very difficult to transfer a diagnostic specimen from a remote area to a more specialized laboratory and ensure diagnostic accuracy; this is especially relevant given the potential for delays and temperature fluctuation during international shipping. There exists a need in clinical diagnostics for a reliable method for the storage and transport of sputum and other biological samples such that pathogens can be identified, or quantified, even after significant storage and transport.

In developed countries, sputum samples are transported at 4° C. to the laboratory which adds significantly to overall costs. In many developing countries, due, in part, to cost and lack of infrastructure, sputum specimens are typically transported to laboratories at ambient temperature (i.e., no cold chain maintenance). Even storage of sputum specimens at room temperature for more than 3 days is known to result in significant loss of culture viability and increased contamination rate (Paramasivan et al., 1983). Unfortunately, initial errors made by preliminary microscopic diagnosis may not be known until weeks later, when the clinical signs are more evident (in false negatives). As a result, several groups have tried to develop a method to preserve sputum samples to have them forwarded to larger centers for processing. Holz et al (2001) and Popova et al (2004) demonstrated that samples can be successfully stored frozen for up to 10 days before processing. Kelly et al (2003) and Dorman et al (2010) proposed fixation of sputum in formaldehyde and alcohol, respectively, before processing. However, all these preservation methods can affect the viability of mycobacteria, impacting their subsequent growth and detection in culture media.

The present inventors have developed a chemical collection or transport composition that surprisingly stabilizes tough microorganisms in complex sputum specimens during transport and storage, while maintaining the viability of *Mycobacteria* for diagnostics utilizing smear microscopy, culture, and real-time or quantitative PCR (qPCR). Advantageously, the present transport composition kills the majority of background microorganisms upon contact with sputum. In this example, attenuated *Mycobacterium tuberculosis*-spiked sputum samples were mixed with a sputum transport chemistry (STC) composition and stored at typical ambient temperatures (35° C., room temperature, and 4° C.) for as long as 30 days prior to culture, DNA extraction and qPCR.

Experimental Method

For the present example, frozen raw sputum samples from healthy TB-negative patients were kindly donated by the Foundation for Innovative Diagnostics (FIND) Tuberculosis Specimen Bank. Using culture and smear analysis, FIND categorized the patient samples as 'Smear negative, Culture negative.'

Preparation of *Mycobacterium tuberculosis*-Spiked Biological Samples

Raw sputum samples, confirmed as TB-negative were shipped frozen from FIND. Sputum samples were thawed slowly on ice and pooled to form two 8 mL samples. To safely simulate tuberculosis-positive sputum, sputum was spiked with a moderate concentration of attenuated *M. tuberculosis* H37Ra (aMTB) at $5\times10^6$ colony forming units/mL (cfu/mL). One 8 mL pooled, spiked sample was split equally into three fractions, each fraction was mixed with an equal volume of BD2 buffer (2% SDS, 12 0.5 mM CDTA, 250 mM LiCl, 50 mM glycine, pH 10.5) or Sample Transport Chemistry (STC), and then fractions were held at 4° C., 35° C. or room temperature for up to 30 days. The second 8 mL pooled, spiked sample was not treated, i.e., left neat, split equally into three fractions, and then held at 4° C., 35° C. or room temperature, for up to 30 days.

At indicated time points (T=0, 7 days, 14 days and 30 days), aliquots were removed from the fractions stored at various temperatures. Aliquots were used to inoculate cultures, or DNA was extracted from aliquots utilizing 3 different methodologies (Periodate, Guanidine thiocyanate, Bead-beating), and the extracted DNA was quantified using qPCR and *Mycobacterium*-specific primers. All aMTB-spiked fractions were stored at 35° C., 4° C. and room temperature (RT) for 7, 14, and 30 days prior to culture and qPCR.

Culture Conditions for MTB-Spiked Sputum Fractions

At each time point, an aliquot (400 µL) from each of the fractions was isolated for culture.

For BD2 buffer-treated fractions, 400 µL aliquots were centrifuged at 5,000 rpm for 20 minutes to pellet bacteria. Supernatants were discarded and pellets were resuspended in 400 µL sterile PBS, and vortexed until thoroughly mixed.

For non-treated (NT) fractions, 400 µL aliquots were mixed with 200 µL fresh NaOH (2%)-NALC (0.5%)-citrate (1.45%) and incubated at room temperature for 15 minutes. 600 µL of sterile PBS was added to each tube and centrifuged at 5,000 rpm for 20 minutes. The supernatant was discarded and the pellet was resuspended in 400 µL sterile PBS, and vortexed until thoroughly mixed.

For BD2 buffer-treated and non-treated fractions, 100 µL of resuspended bacteria was then plated directly onto three LB plates using the spread plate method and incubated at 37° C. At approximately day 4, the number of colonies were counted.

Extraction of DNA from aMTB-Spiked BD2 Buffer-Treated Sputum Using the Periodate Method 1. At each of the indicated times and temperatures (0, 7, 14, and 30 days at 35° C., 4° C. and RT), a 400 µL aliquot from BD2 buffer-treated fraction was transferred to a fresh tube and centrifuged at 5,000 rpm for 20 minutes to pellet bacteria.
2. Supernatant was discarded and the pellet was resuspended in 400 µL BD2 buffer.
3. Sodium (meta)periodate was added to a final concentration of 15 mM and vortexed to mix.
4. The mixture was incubated at 70° C. in a water bath for 20 minutes.
5. Samples were cooled at room temperature for 2 minutes.
6. 1M Tris buffer (pH 7) was added to a final concentration of 50 mM.
7. The mixtures were incubated at room temperature for 10 minutes.
8. 3M potassium acetate (pH 5.5) was added to a final concentration of 150 mM, vortexed to mix.
9. The mixtures were incubated on ice for 10 minutes and then centrifuged at 13,000 rpm for 5 minutes.
10. The supernatant was transferred to a clean, labeled tube and the pellet was discarded.
11. Two volumes of room temperature 95% ethanol was added to the supernatant in the tube and the tube was inverted 20 times to mix.
12. The mixture was incubated at room temperature for 10 minutes to precipitate DNA and then centrifuged at 15,000 rpm for 2 minutes to pellet DNA.
13. The supernatant was gently removed and discarded taking care not to disturb the pellet.
14. The pellet was dissolved in 200 µL TE (the mixture was vortexed briefly to fully resuspend DNA).

Extraction of DNA from aMTB-Spiked NT Sputum Using Guanidine Thiocyanate Method

1. Freshly prepared and autoclaved 4% solution of sodium hydroxide (NaOH).
2. Freshly prepared and autoclaved 2.9% sodium citrate solution.
3. Equal volumes of the NaOH and sodium citrate solution were mixed and N-acetyl-L-cysteine (NALC)

powder was added to achieve a final concentration of 0.5%; the solution was mixed well and used the same day.

4. At each of the indicated times and temperatures (0, 7, 14, and 30 days at 35° C., 4° C. and RT), a 400 µL aliquot from the NT fraction was transferred to a fresh tube and 200 µL of the fresh NaOH-NALC-citrate was added; the tube was vortexed well to mix.
5. The mixture was incubated at room temperature for 15 minutes before adding 600 µL sterile PBS and centrifuging at 5,000 rpm for 20 minutes, to pellet bacteria.
6. The supernatant was discarded and 400 µL sterile PBS was added to the pellet; the tube was vortexed to mix.
7. The mixture was centrifuged at 5,000 rpm for 20 minutes to re-pellet bacteria.
8. The supernatant was discarded and the pellet was resuspended in 400 µL sterile PBS.
9. To 200 µL of resuspended pellet, 1 mL DNAzol Reagent (a guanidine thiocyanate-detergent lysing solution, Cat. No. 10503-027, Life Technologies) was added and the mixture was pipetted up and down to lyse the cells; then 0.5 mL of 100% ethanol was added and the tube was inverted 10 times to mix.
10. The mixture was incubated at room temperature for 3 minutes and then centrifuged at 14,000 rpm for 2 minutes to pellet DNA.
11. The DNA pellet was washed twice with 1 mL of 75% ethanol.
12. All traces of ethanol were removed and the DNA pellet was dissolved in 200 µL of 8 mM NaOH.

Extraction of DNA from aMTB-Spiked NT Sputum Using "Bead-Beating" Method ("Standard of Care")

1. At each of the indicated times and temperatures (0, 7, 14, and 30 days at 35° C., 4° C. and RT), a 400 µL aliquot was transferred from the NT fraction to a fresh tube and 200 µL of fresh NaOH-NALC-citrate was added; the tube was vortexed well to mix.
2. The mixture was incubated at room temperature for 15 minutes before adding 600 µL sterile PBS and centrifuging at 5,000 rpm for 20 minutes to pellet bacteria.
3. The supernatant was discarded and 400 µL sterile PBS was added to the pellet; the tube was vortexed to mix.
4. The mixture was centrifuged at 5,000 rpm for 20 minutes to re-pellet bacteria.
5. The supernatant was discarded and the pellet was resuspended in 400 µL sterile PBS.
6. Two hundred µL of resuspended bacteria was heated at 80° C. for 1-2 hours.
7. Two hundred mg of 105-150 micron glass beads was added to the heated bacteria mixture.
8. The mixture containing the glass beads was vigorously shaken for 2 cycles of 1 minute each using a Mini-BeadBeater™ (BioSpec Products); each cycle was followed by 1 minute on ice.
9. The sample was heated at 95° C. for 2 minutes prior to PCR.

rtPCR Conditions

In this example, DNA isolated from aMTB-spiked sputum aliquots was subjected to an rtPCR assay (qPCR) specific for Mycobacterium, the RD4 Taqman Real-time PCR assay. Primers for RD4 were as follows: RD4-forward 5'-CCA CGA CTA TGA CTA GGA CAG CAA-3' and RD4-reverse 5'-AAG AAC TAT CAA TCG GGC AAG ATC-3' (Halse et al. (2011)). Threshold cycle ($C_t$) values less than 37 were reported as positive, and samples with values greater than 37 were retested; if the results were the same, the result was reported as negative, and if they were not, they were reported as inconclusive.

Results and Discussion

Generally, in the standard of care (SOC) scenario, sputum specimens remain untreated (NT) during collection and transport to the laboratory. Upon receipt in the laboratory, sputum undergoes liquefaction and decontamination with the addition of NALC-NaOH-citrate, followed by culture. The present example demonstrates that attenuated MTB remained viable to some degree in untreated sputum maintained at room temperature and 4° C. for up to 30 days, but not when maintained at 35° C., since subsequent cultures showed no growth (NG) (Table 1).

When practising the method as described in the present application, sputum specimens would ideally be mixed with Sample Transport Chemistry (e.g. BD2 buffer) at the point of collection, and maintained in this state throughout transport and storage, until processed at the laboratory. At no point would NALC-NaOH-citrate treatment be employed. Similar to NT sputum, this example demonstrated that aMTB remained viable in STC alone for at least 30 days at room temperature and 4° C. (Table 1). Both methods, STC and NT, failed to support aMTB viability at 35° C. for 7 to 30 days. It has been surprisingly found that STC can be added to sputum at the point of collection (T=0), to immediately liquefy specimens and eliminate or minimize growth of background flora, before it has an opportunity to overtake the specimen, without negatively impacting the viability of the target organism, Mycobacterium, if present, for at least 30 days.

TABLE 1

Viability of Mycobacterium in culture

| Collection & Transport Method/Chemistry | Hold Temp | Viability in Culture After Hold Time | | | |
|---|---|---|---|---|---|
| | | Day 0 | Day 7 | Day 14 | Day 30 |
| Sample Transport Chemistry | RT | V | V | V | V |
| | 4° C. | V | V | V | V |
| | 35° C. | V | NG | NG | NG |
| Standard of Care | RT | V | V | V | V |
| | 4° C. | V | NG | V | V |
| | 35° C. | V | NG | NG | NG |

V: Viable aMTB with no contamination
NG: No growth up to 42 days at 35° C.

In aMTB-spiked sputum specimens collected and stored in STC at 35° C., 4° C. and room temperature for up to 30 days, real-time PCR showed that the concentration of subsequently extracted aMTB DNA remained stable, irrespective of the storage temperature and time (see Table 2). Comparable to heat and physical disruption of aMTB with bead-beating, the periodate treatment was found to be equally effective at releasing functional, qPCR-quality DNA from attenuated Mycobacteria tuberculosis. In contrast, extraction using DNAzol (guanidine thiocyanate-detergent) treatment proved to be dramatically less effective than either periodate or bead-beating methods for releasing DNA. Notably, STC in combination with periodate increased the sensitivity of the Mycobacterium-specific assay by 1 log (3+$C_t$ values), compared to SOC method in combination with the DNAzol treatment. Hence, the standard NALC-NaOH-citrate laboratory procedure, followed by mechanical bead-beating, can be successfully substituted by STC, followed by periodate treatment during processing of specimens in the laboratory. Importantly, STC can be mixed with sputum at the point of collection to control background flora without negatively impacting *Mycobacterium* viability.

TABLE 2 qPCR of DNA extracted from STC- and SOC-treated, aMTB-spiked sputum.

| Collection & Transport Method/ Chemistry | Extraction/ Treatment | Hold Temp | $C_T$, Day 0 | $C_T$, Day 7 | $C_T$, Day 14 | $C_T$, Day 30 |
|---|---|---|---|---|---|---|
| Sample Transport Chemistry (STC) | Periodate | 35° C. | 25.74 | 24.93 | 25.3 | 25.94 |
| | | 4° C. | 25.77 | 25.63 | 25.54 | 25.74 |
| | | RT | 25.64 | 25.17 | 25.75 | 25.32 |
| Standard of Care (SOC) | DNAzol (guanidine thiocyanate-detergent) | 35° C. | 29.76 | 30.68 | 28.79 | 31.04 |
| | | 4° C. | 30.3 | 29.93 | 29.58 | 32.52 |
| | | RT | 29.72 | 29.24 | 31.11 | 30.74 |
| | Bead-beat | 35° C. | 24.22 | 25.75 | 26.74 | 25.95 |
| | | 4° C. | 24.3 | 23.49 | 25.56 | 24.8 |
| | | RT | 24.19 | 24.07 | 25.32 | 26.32 |

Example 2: Sample Transport Chemistry Liquefies Sputum Upon Contact

Sputum from humans is used to diagnose tuberculosis and detect infection in cystic fibrosis patients. Bacteria are not uniformly distributed in such a highly viscous specimen, which poses a problem for the acid fast staining typically used to identify *Mycobacteria*. Remarkably, this technique for diagnosing tuberculosis has been found to have only about 50% sensitivity, i.e., there is an equal chance of detecting the presence of TB as not detecting it when the patient actually has the disease. This lack of sensitivity is due to the inability of existing sample preparation protocols to generate a sample in which the bacteria is uniformly distributed such that there is an equal probability of obtaining *Mycobacteria* for staining from any portion of the specimen. Hence, liquefaction and homogenization of sputum specimens is critical to ensure accurate, representative sputum cultures and molecular diagnostics.

Liquefaction is determined by a reduction in viscosity, the ability to easily pipette the sample, and the complete loss of dense clumps. A variety of mucolytic agents have been previously used to liquefy sputum specimens, including, for example, pancreatin, pancreatin-trypsin, and sodium 2-ethylhexyl sulphate (Tergemist), amylase, N-acetyl-L-cysteine (NALC), and dithiothreitol (DTT, Sputolysin) (Hammerschlag et al., 1980). NALC, which is one of the more popular liquefying agents, has appreciable inhibitory activity in vitro against *Pseudomonas aeruginosa*, the principal pathogen in the sputum of most cystic fibrosis (CF) patients. Also, cells that are incompletely released from mucus by these mucolytic agents tend to stain darkly, making correct identification difficult.

Surprisingly, during handling of mucoid sputum samples, the present inventors observed that STC alone (BD2 buffer: 2% SDS, 12 0.5 mM CDTA, 250 mM LiCl, 50 mM glycine, pH 10.5) was sufficient for sputum liquefaction. A reducing agent, such as NALC or DTT, was not required and the degree of liquefaction was comparable to that obtained using the current standard of care, 3.5% sodium hydroxide (NaOH) treatment method. Unlike NaOH-NALC-citrate, which needs to be made fresh every 12 to 24 hours, BD2 buffer is stable at room temperature for months. The visual observation of liquefaction was confirmed by analyzing high technical replicates for DNA yield using PicoGreen® fluorescent dye and a fluorometric method, as well as qPCR with primers specific for 16S rRNA gene.

Materials & Methods

In this example, two mL of sputum from a healthy donor was pooled and vortexed. An equal volume of BD2 buffer was added, mixed by inversion, and incubated at room temperature for 15 minutes. At this point, the sputum was completely fluidized. In order to extract nucleic acid, sputum was treated with proteinase K (160 μg) and incubated at 50° C. for 2 hours. Following this incubation, 10×200 μL aliquots were removed into fresh tubes as high technical replicates. To each 200 μL aliquot, 10 μL of 3M potassium acetate (150 mM final) was added and tubes were held on ice for 10 min. Following centrifugation at 13,000 rpm for 5 min, the supernatant was transferred to fresh tubes. DNA was precipitated with 2 volumes of room temperature 95% ethanol. After 15 minutes at room temperature, DNA was pelleted in a 2 minute centrifugation step at 13,000 rpm. The DNA pellet was dissolved in 100 μL of TE buffer (pH 7.1).

Fluorometric Determination of DNA Concentration

DNA from 10 purified samples was quantified using PicoGreen® Fluorescent dye (200×; Invitrogen, Cat. No. P7581); Lambda DNA (Invitrogen, Cat. No. 25250-010) was used to generate a standard curve [in triplicate; 0-50 ng/μL]. PicoGreen® is a fluorescent double-stranded DNA-binding dye (485 nm Excitation/535 nm Emission) that enables sensitive quantitation of sub-nanogram amounts of double-stranded DNA (dsDNA). Aliquots of each purified sample and Lambda DNA standards were processed in a black flat-bottomed 96 well microplate (Greiner Bio-One, Cat. No. 655209) and fluorescence was measured using an Infinite M200 microplate reader (TECAN).

rtPCR Conditions

DNA extracted from 10 sputum aliquots was subjected to an rtPCR assay (qPCR) specific for 16S rRNA gene. Primers for 16S rRNA gene are as follows: BacrRNA173-F 5'-ATTACCGCGGCTGCTGG-3' and BacrRNA173-R 5'-CCTACGGGAGGCAGCAG-3'. Each PCR reaction contained 2 μL template, 2.5 μL of 1 mg/mL bovine serum albumin (BSA), 2.5 μL of 10×PCR Buffer, 1.25 μL of 50 mM $MgCl_2$, 0.5 μL of 10 mM dNTPs, 0.5 μL of 10 pMol forward primer, 0.5 μL of 10 pMol reverse primer, 0.5 μL of 0.5 μM Syto 9, 0.2 μL of 5 U/μL Taq Polymerase, 12.3 μl of water. Highly purified DNA from *E. coli* served as a reference for PCR analysis. Negative controls included reactions in which no template DNA was added. The $C_t$ value refers to the fractional cycle number at the point where the amplification curve crosses a threshold of detection. The Rotorgene instrument software set a threshold line and calculated the Ct values for each sample. Ct values are inversely proportional to the amount of DNA in a sample; a decrease in one Ct value corresponds to a doubling in the amount of DNA detected.

Results and Conclusions

TABLE 3

High technical replicate DNA yield from sputum.

| Aliquot | DNA concentration (ng/μL) | $C_t$ value |
|---|---|---|
| 1 | 54.68 | 15.10 |
| 2 | 65.04 | 15.40 |

TABLE 3-continued

High technical replicate DNA yield from sputum.

| Aliquot | DNA concentration (ng/μL) | $C_t$ value |
|---|---|---|
| 3 | 66.13 | 15.40 |
| 4 | 62.23 | 15.30 |
| 5 | 71.03 | 15.20 |
| 6 | 63.30 | 15.30 |
| 7 | 68.40 | 15.40 |
| 8 | 67.43 | 15.20 |
| 9 | 67.53 | 15.30 |
| 10 | 71.73 | 15.20 |
| Average: | 65.75 | 15.28 |
| Standard Deviation: | 4.92 | 0.10 |
| Median: | 66.78 | 15.30 |

Complete reduction of the viscosity of sputum is critical to reducing sampling error and increasing the accuracy of cultures. Experimentation has shown that sputum was liquefied by the present chemistry in ratios of 5:1 to 1:5 (sputum:STC).

The present example demonstrates that highly viscous sputum was completely liquefied by a single, 15 minute, room temperature treatment with an equal volume of STC. Each aliquot withdrawn from STC-treated sputum and analyzed was essentially identical in total DNA concentration, as shown by the PicoGreen fluorometric method (Table 3). This means that there is a uniform distribution of DNA (from any source) homogeneously distributed throughout the sample, which is indicative of liquefaction. Also, qPCR using bacteria-specific primers indicated that each technical replicate contained the same amount of bacterial DNA. Hence, a brief exposure to STC was sufficient to uniformly distribute endogenous bacteria throughout the specimen.

The present example demonstrates that STC can be generally mixed with specimen at the point of sputum collection to generate a liquefied sample at collection. However, STC can also be added to specimens in the laboratory prior to processing (e.g., acid fast staining) or culture, to provide a liquefied sample at the time of testing.

The results herein further demonstrate that the STC composition and the method described herein did not compromise the integrity of the tests, while still ensuring the speed and accuracy necessary for implementation in the field. This simple, rapid, inexpensive sputum sample processing methodology can make available/accessible more *Mycobacteria*, when present, for various detection methodologies in both resource-rich and -poor settings, preventing further dissemination of disease.

Example 3: Compatibility of Sample Transport Chemistry in Tuberculosis Diagnostics Using Smear Microscopy, Culture and Molecular Diagnostic Assays Globally, about 2 billion people are infected with the potentially highly infectious *M. tuberculosis* ("MTB"). Every year almost 9 million people develop active disease, and 2 million people die of the illness. Given the infectious nature of MTB, fast and accurate diagnosis is an important element of MTB treatment and disease control.

Four common first-line drugs used in anti-tuberculosis therapy are Isoniazid (INH), Rifampin (RIF), Ethambutol (EMB), and Pyrazinimide (PZA). MTB strains, however, can become resistant to one or more of the drugs, making cure difficult to achieve. RIF resistance is most commonly seen in multi-drug resistant (MDR-TB) strains and has a reported frequency of greater than 95% in such isolates (Morris et al, 1995). MDR-TB is defined as a tuberculosis disease caused by a bacterial strain that is resistant to at least INH and RIF. Resistance to RIF or other first-line drugs usually indicates the need for full susceptibility testing.

In this example, an independent diagnostics laboratory, All India Institute of Medical Sciences (AIIMS, New Delhi, India), with access to human TB-positive sputum specimens, was engaged to compare side-by-side the current gold standard method for diagnosing *M. tuberculosis* from sputum to the present invention in which raw sputum samples were collected into Sample Transport Chemistry (STC). Testing included 1) smear microscopy, 2) MGIT culture, 3) Cepheid GeneXpert® (PCR-based detection of *M. tuberculosis* and rifampin (RIF) resistance), and 4) laboratory developed multiplex PCR (LDMP) assay (Gopinath and Singh, 2009) for diagnosing *Mycobacterium* infections.

The Xpert MTB/RIF Assay for use with the Cepheid GeneXpert system is a semi-quantitative, nested real-time PCR in vitro diagnostic test for the detection of 1) *Mycobacterium tuberculosis* complex DNA in sputum samples or concentrated sediments prepared from induced or expectorated sputa that are either acid-fast bacilli (AFB) smear positive or negative; and 2) Rifampin-resistance associated mutations of the rpoB gene in samples from patients at risk for rifampin resistance.

Experimental Method

Processing of Raw Sputum Specimens and Four Diagnostic Tests

Raw sputum samples were collected from six patients with confirmed TB or high probability of active infection with MTB. Specimens 4 mL) were manually split by pipette into 2 portions (2 mL each) and treated with an equal volume of freshly prepared 4% NaOH/0.5% NALC (gold standard) or STC (BD2 buffer composed of 2% SDS, 12 0.5 mM CDTA, 250 mM LiCl, 50 mM glycine, pH 10.5), prior to being evaluated by culture, AFB smear and two molecular diagnostic assays.

Following the addition of either NaOH/NALC or STC, each portion was treated as follows:
1. Mixtures were vortexed for 10-15 seconds.
2. Mixtures were allowed to stand for 15 minutes at room temperature; 20-25 minutes for highly mucoid samples.
3. Tubes were filled to 50 mL mark with phosphate buffer (pH 6.8), then inverted several times to mix thoroughly before centrifuging at 3,000-3,500 RCF for 15 minutes.
4. The supernatant was carefully poured off and the pellet was resuspended in 1.25 mL sterile phosphate buffer, which was aliquoted as follows:
   a. Aliquot 1: 300 μL
      i. Added 300 μL of sterile phosphate buffer (600 μL total volume).
      ii. Acid-fast bacilli (AFB) Smear Examination (100 μL)
         1. Performed smear according to established laboratory protocols. Smear was done prior to decontamination of sputum (Smear Direct) and after decontamination (DC) with either NaOH/NALC or STC (Smear DC). Smear scoring: 1+ denotes a low positive sample, 2+ denotes a moderate positive sample, 3+ denotes a high positive sample.

iii. BACTEC™ MGIT-960 Culture (500 µL)
     1. Inoculated into BACTEC™ MGIT tubes under sterile conditions in biosafety cabinet type 2.
     2. Loaded inoculated MGIT-960 tubes in the BACTEC™ MGIT-960 system and growth was continuously monitored up to 42 days in the fluorescence units and tubes flashed positive after reaching a cut-off growth. Status of one MGIT culture was not reported.

b. Aliquot 2: 250 µL
   i. Added 250 µL of sterile phosphate buffer (500 µL total volume).
   ii. Laboratory Developed Multiplex PCR (LDMP) assay
     1. Followed AIIMS protocol for purifying DNA for analysis by LDMP assay (Gopinath and Singh, 2009).
     2. Briefly, cell walls were lysed with lysozyme, followed by proteinase K digestion and sodium dodecyl sulphate treatment of proteins.
     3. NaCl and hexadecyltrimethylammonium bromide were used to precipitate proteins and macromolecules.
     4. Nucleic acids were recovered from aqueous phase after extraction with chloroform and isoamyl alcohol.
     5. DNA was precipitated overnight with isopropanol at −20° C.
     6. Pellet was washed with ethanol and reconstituted with 50 µL of TE buffer; 10 µL was used in multiplex PCR.
     7. In multiplex PCR (Gopinath and Singh, 2009), three primer sets were used, including *Mycobacterium* genus specific primers (hsp 65) (Telenti et al., 1993), *M. avium* complex specific (MAC) primers (Park et al., 2000) and a novel *M. tuberculosis* (MTB) complex-specific set of primers targeting cfp 10 or esat (Gopinath and Singh, 2009).

c. Aliquot 3: 300 µL
   i. Added 300 µL of sterile phosphate buffer (600 µL total volume).
   ii. Cepheid Xpert MTB/RIF Assay
     1. Added 1.8 mL Cepheid SR buffer (1:3 ratio).
     2. Tested according to Cepheid GeneXpert® MTB/RIF Assay for Sputum Sediments (Protocol H.1).
     3. GeneXpert real-time PCR gives 2 results: 1) *M. tuberculosis* Positive/Negative, and 2) rifampin (RIF) antibiotic Sensitivity or Resistance (Sens/Res) (Table 4).

d. Aliquot 4: 250 µL
   i. Transferred 250 µL of sample to a 2 mL spin tube.
   ii. Added 250 µL of STC (500 µL total volume).
   iii. DNA extraction protocol for STC-treated samples:
     1. Added sodium (meta)periodate to a final concentration of 30 mM; vortex to mix.
     2. Incubated at 70° C. for 20 minutes; cooled samples to room temperature.
     3. Added 1M Tris buffer (pH 7) to a final concentration of 50 mM; vortexed to mix.
     4. Added 3M potassium acetate (pH 5.5) to a final concentration of 150 mM; vortexed to mix.
     5. Incubated on ice for 10 minutes.
     6. Centrifuged at 13,000 rpm for 5 minutes.
     7. Transferred supernatant to a clean, labelled tube. Discarded pellet.
     8. Added 2 volumes of room temperature 95% ethanol.
     9. Inverted 20 times to mix.
     10. Incubated samples at room temperature for 15 minutes.
     11. Centrifuged at 15,000 rpm for 2 minutes to pellet DNA.
     12. Gently removed and discarded supernatant taking care not to disturb the pellet.
     13. Dissolved the pellet in 100 µL of TE.
     14. Vortexed briefly and let stand at room temperature for at least 30 minutes.
     15. Stored purified DNA at room temperature or −20° C.

Results and Conclusions

Brief exposure of sputum specimens to STC successfully liquefied and decontaminated specimens from all 6 patients tested (Table 4) at a level approximately equivalent to that obtained using NaOH/NALC treatment. Following decontamination with NaOH/NALC or STC, inoculated cultures subsequently showed no signs of contamination, indicating that STC was equally effective at killing background microflora in clinical specimens.

Smear analysis produced the same diagnostic result (1+ to 3+), independent of the decontamination method (Table 4), indicating that STC didn't alter the acid-fast staining properties of *Mycobacteria*. Hence, standard laboratory practices for detecting *Mycobacteria* by microscopy can be readily applied using sputum specimens collected directly into STC.

*Mycobacteria* were cultured from all 6 patient samples following the liquefaction and decontamination of sputum with NaOH/NALC or STC. STC did not adversely impact the viability of *Mycobacteria* in culture and the results obtained were comparable to those obtained using conventional NaOH/NALC treatment (Table 4).

Molecular diagnostic test results were also equivalent for NaOH/NALC and STC treated patient samples. Nested real-time PCR analysis using the Cepheid GeneXpert® system indicated that all 6 patients were positive for *Mycobacterium tuberculosis* and sensitive to rifampin (Table 4). AIIMS Laboratory Developed Multiplex PCR assay confirmed the 6 patients were in fact positive for *M. tuberculosis* at the genus and species level, as well as negative for *Mycobacterium avium* complex (Table 4). STC treated sputum samples were also compatible with AIIMS established TB testing algorithm, a LDMP assay in which nucleic acids were recovered from specimens using a standard chloroform/isoamyl alcohol purification method.

The present example demonstrates that raw sputum specimens liquefied and decontaminated with STC can be used successfully in standard diagnostic methods for detection and characterization of mycobacterial infection, using the full suite of current methodologies, including culture, microscopical identification of acid-fast bacilli (AFB) and molecular diagnostic tests. These STC treated samples can also be used in PCR-based tests used for the aetiological mycobacterial species in order to administer the appropriate therapy and for better patient management.

TABLE 4

Culture, AFB Smear and Molecular Diagnostic Assay Results for *M. tuberculosis*

| Sample # | Sputum Treatment Method | AFB Smear Direct | AFB Smear DC | MGIT Culture Status | Cepheid Xpert MTB | Cepheid Xpert RIF | AIIMS DNA Extraction & LDP Assay (hsp/esat/MAC) |
|---|---|---|---|---|---|---|---|
| 1 | NaOH/NALC | 1+ | 1+ | Pos | Pos | Sens | +/+/− |
|   | STC | 1+ | 1+ | Pos | Pos | Sens | +/+/− |
| 2 | NaOH/NALC | 1+ | 1+ | Pos | Pos | Sens | +/+/− |
|   | STC | 1+ | 1+ | Pos | Pos | Sens | +/+/− |
| 3 | NaOH/NALC | 1+ | 1+ | Pos | Pos | Sens | +/+/− |
|   | STC | 1+ | 1+ | Pos | Pos | Sens | +/+/− |
| 4 | NaOH/NALC | 3+ | 3+ | Pos | Pos | Sens | +/+/− |
|   | STC | 3+ | 3+ | Pos | Pos | Sens | +/+/− |
| 5 | NaOH/NALC | 2+ | 2+ | Pos | Pos | Sens | +/+/− |
|   | STC | 2+ | 2+ | Not reported | Pos | Sens | +/+/− |
| 6 | NaOH/NALC | 1+ | 1+ | Pos | Pos | Sens | +/+/− |
|   | STC | 1+ | 1+ | Pos | Pos | Sens | +/+/− |

Example 4: Sputum Microbiome is Stable in Sample Transport Chemistry

In the present example, the Sample Transport Chemistry (STC) compositions were mixed with raw, pooled sputum (TB-free) to assess liquefaction and decontamination of sputum, as well as stability of the endogenous microbiome with prolonged storage at room temperature. As a control for the industry standard use of sodium hydroxide in standard sputum decontamination/liquefaction procedures, sputum was also stored long-term following a brief treatment with sodium hydroxide.

Experimental Method

Treatment of Sputum Specimens

Three TB-negative sputum specimens (kindly donated by FIND Tuberculosis Specimen Bank) were pooled and split evenly into three 1 mL aliquots. An equal volume of BD2 buffer (2% SDS, 12.5 mM CDTA, 250 mM LiCl, 50 mM glycine, pH 10.5), BD3 buffer (4% SDS, 50 mM CDTA, 250 mM LiCl, 140 mM LiOH, pH 6.8) and sodium hydroxide (NaOH, 3.5%) was added to the three sputum aliquots and mixed. Within 15 minutes at room temperature, all three mixtures were equally liquefied, where liquefaction was qualitatively determined by a reduction in viscosity, the ability to easily pipette the sample, and the complete loss of dense clumps.

The NaOH-treated aliquot was pelleted by centrifugation (3,000 rpm for 15 minutes), supernatant was discarded, and the pellet was brought up in PBS and stored at 4° C. for up to 28 days. BD2- and BD3-treated sputum samples were maintained at room temperature (15-25° C.) for up to 28 days in a biosafety cabinet.

DNA Purification

1. At 0, 1, 7, 21 and 28 days post-treatment (above), 200 µL aliquots from each mixture were pulled for purification of DNA.
2. 81 mg of Proteinase K was added to each aliquot and incubated overnight at 50° C.
3. Each of these aliquots were split into two 100 µL aliquots, one for extraction including sodium (meta) periodate (NPI) and the other without NPI.
4. To the +NPI aliquot, NPI was added to a final concentration of 15 mM, incubated at 70° C. for 20 minutes, and cooled at room temperature.
5. 1 M Tris pH 7.1 was added to all samples to a final concentration of 100 mM; incubated at room temperature for 5 minutes.
6. Added 3 M potassium acetate to all samples to a final concentration of 150 mM.
7. Incubated on ice for 10 minutes.
8. Centrifuged at 13,200 rpm for 5 minutes; transferred supernatant to a fresh tube and discarded the pellet.
9. Added 2 volumes of room temperature 95% ethanol to supernatant.
10. Incubated at room temperature for 15 minutes.
11. Centrifuged at 13,200 rpm for 2 minutes; discarded the supernatant.
12. Resuspended the DNA pellet in 50 µL TE buffer (pH 7.1).

Denaturing Gradient Gel Electrophoresis

To accurately and reproducibly evaluate the stability of the sputum microbiome in the present compositions, a relatively new method called Denaturing Gradient Gel Electrophoresis (DGGE) was utilized. This method is based on the idea that if one takes a variable region of the bacterial 16S rRNA gene (in this case the V3 region) and amplifies it using PCR and primers on the flanking conserved region, that amplicons will have a melting point unique to the species of bacteria (even single nucleotide differences will affect the melt and thus give a different profile).

When this method is applied to a sample containing multiple species of bacteria, the amplification using conserved primers will result in an array of amplicons, all of which are roughly the same length, but have a different nucleotide make-up in the non-conserved area. Next, these amplicons are run on a gel that contains a gradient of denaturing solution (urea and formamide). The amplicons will denature at different stages on the gel, depending on their nucleotide make-up, thus giving a resolution of all the species that were present in the sample.

In order for the DNA amplicons to not denature to single-stranded form, a ~30 nucleotide CG clamp was added to the forward primer which retards the migration of the amplicons on the gel once the variable section has denatured. In general, a 40%-60% denaturing gradient on the gel provides good resolution of the bands, while capturing most of the sputum species. The gel is run at a constant 55° C. in order to facilitate denaturing of the amplicons and also keep the gel at equal temperature throughout the run.

PCR-DGGE was carried out according to the procedure described below.

PCR Amplification for DGGE (Using 16S Primers with 5'Clamp on Forward Primer)

a. 2 µL of 10 ng/µL purified DNA was added into 12-strip PCR tubes.
b. Master Mix was prepared (98 µL/reaction): 76.7 µL water, 10 µL 10×PCR Buffer, 4 µL 50 mM $MgCl_2$, 2.5 µL 10 mM dNTPs, 2 µL 10 pmol Rev Primer (PPUN518R, 5'-ATTACCGCGGCTGCTGG-3'), 2 µL 10 pmol Fwd Primer (PRBA338F, 5'-CGCCCGCG CGCGGCGGGCGGGGCGGGGGCACGGGGGGAC TCCTACGGGAGGCAGC AG-3'), and 0.8 µL 5 U/µL Taq.
c. 98 µL master mix was added to each tube.
d. PCR was run on conventional PCR machine: 1 cycle at 92° C. for 2 minutes; 28 cycles at 92° C. for 60 seconds, 55° C. for 30 seconds, 72° C. for 60 seconds; followed by 1 cycle at 72° C. for 6 minutes.

DGGE of PCR Amplicons a. Stock solutions were prepared for an 8% Acrylamide/Bis gel in 40% and 60% denaturing solutions:

|  | 40% | 60% |
| --- | --- | --- |
| 40% Acrylamide/Bis | 20 mL | 20 mL |
| 50× TAE Buffer | 2 mL | 2 mL |
| Formamide (deionized) | 16 mL | 24 mL |
| Urea | 16.8 g | 25.2 g |
| $ddH_2O$ | Up to 100 mL | Up to 100 mL | b. The glass plates and spacers were assembled according to the instruction booklet for the DCode system (Bio-Rad).
c. To prepare and pour an 8% Acrylamide/Bis gel with a parallel gradient using 40% and 60% denaturing solutions, the following procedure was used:
20 mL of 40% and 60% denaturing solutions were measured into 2 separate beakers labeled "low density" and "high density," respectively.
200 µl of 10% ammonium persulfate (APS) was added to each solution.
20 µL of TEMED was added to each solution.
The solutions were mixed well by swirling.
Each solution was filled into a separate 20 mL syringe.
The syringes were attached to the gel loading apparatus where specified "low density" or "high density" for top filling.
Note: The volume adjustment settings for a 16×16 cm gel with 1.0 mm spacers was 18.5 mL.
The Y tubing was attached to each of the syringes, with a needle on the other end of the tubing.
The needle was placed between the glass plates.
The gel was poured slowly and consistently by turning the wheel so that the gradient had time to even out.
The gel was allowed to polymerize for a few hours.
d. The gel running system was pre-heated with 1×TAE buffer to 55° C.
e. 8 µL of Fermentas 6×loading dye was added to 42 µl of PCR product.
f. The gel was run for 5 minutes at 200 V before turning on the recirculation pump in order to get the samples out of the wells and into the gel.
g. The gel was run for 14 hours at 70 V with the recirculation pump on.
h. The gel was stained in 1× Sybr Gold for 30 minutes (250 mL 1×TAE+25 µL 10,000×SybrGold).
i. The gel was destained in 1×TAE for 5 minutes.
j. Images were taken under UV light.

16S rRNA gene PCR was performed using universal primers (V3 region) followed by DGGE using the DCode Universal Mutation Detection System (Bio-Rad).

Results and Conclusions

Similar to the standard NaOH treatment, sputa mixed with the present STC compositions (BD2 and BD3 buffer) were rapidly liquefied at room temperature. By visual inspection and handling, the mixtures were reduced in viscosity, easy to pipette, and no dense clumps remained. However, unlike NaOH treatment, which is restricted to a brief 15-20 minutes to avoid killing mycobacteria, sputum can be collected and stored in the STC compositions for days and weeks at room temperature without negatively impacting the ability to culture *Mycobacteria* (see example 1 and 5).

Figure 2:
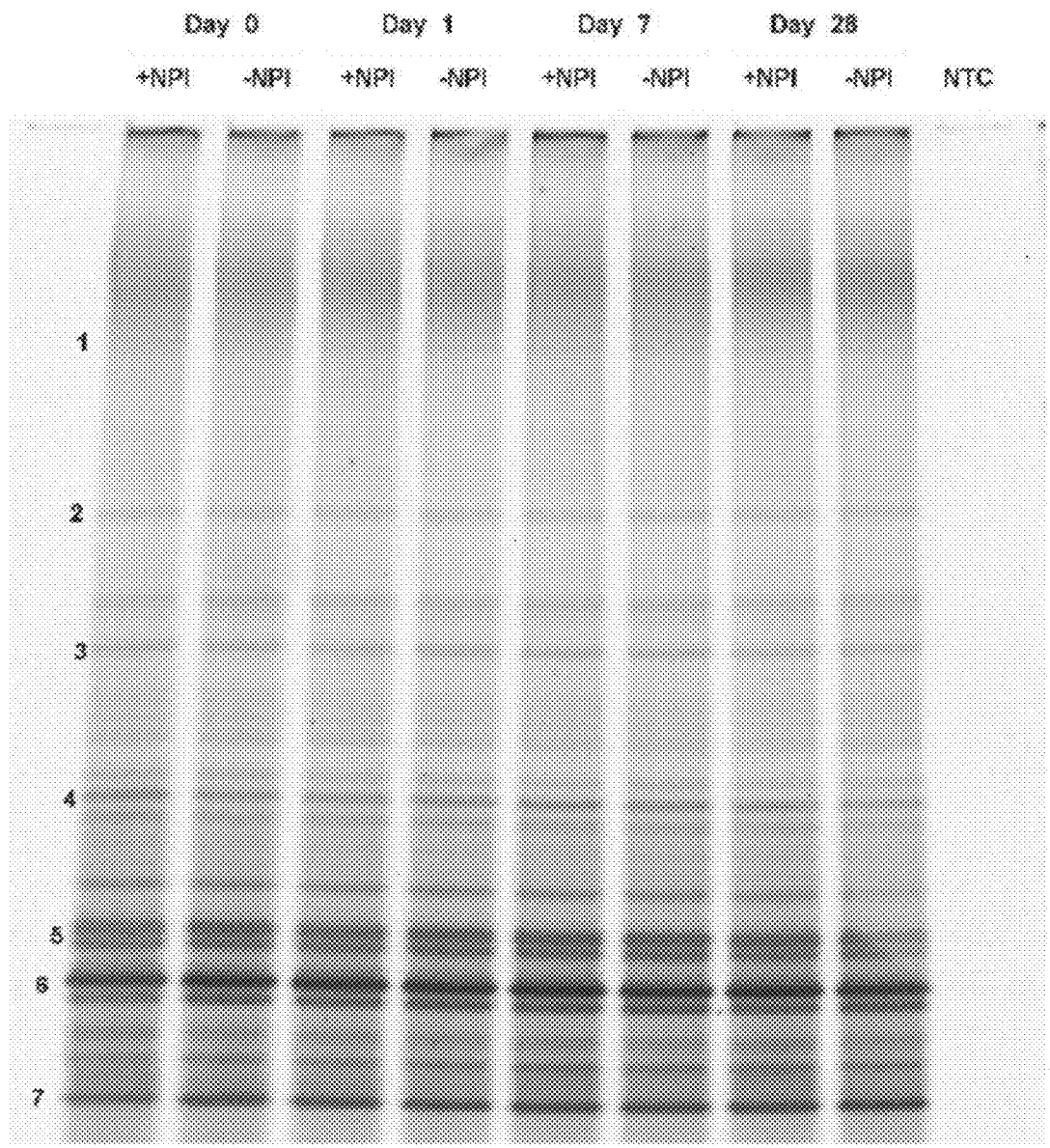
FIG. 2 is a photograph of the gel from DGGE analysis of sputum stored at room temperature in BD3 buffer.
Figure 3:
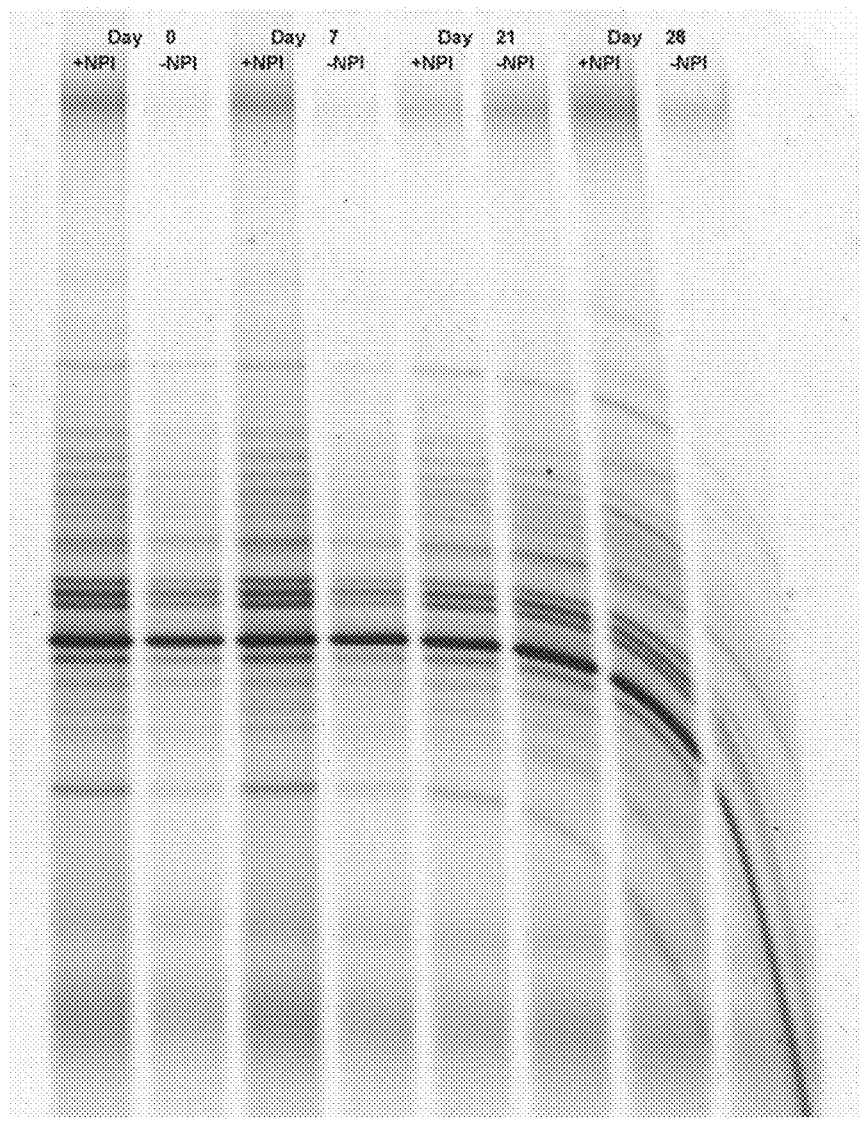
FIG. 3 is a photograph of the gel from DGGE analysis of sputum stored at 4° C. following NaOH treatment.

At day 0, DGGE analysis of bacterial 16S rRNA gene represents the microbiome, or varied population of bacteria, present in this pooled sputum sample at the point of collection (FIGS. 1-3). Over the course of 28 days, the banding pattern resulting from BD2- (FIG. 1)/BD3-(FIG. 2) treated or NaOH— (FIG. 3) treated sputa remained substantially stable, indicating that these mixtures were bacteriostatic at room temperature and 4° C., respectively. For BD2-/BD3-treated sputa, no new bands appeared over time and band intensities remained constant, irrespective of the purification method (+/− NPI) employed.

The number of bacterial 16S rRNA gene bands from both BD2 and BD3-treated sputa were very similar, indicating that both examples of STC compositions preserved bacteria or bacterial DNA to a similar extent during this time period (FIGS. 1 and 2). Interestingly, the DGGE banding pattern resulting from NaOH-treated sputum (FIG. 3) was not identical to that of BD2-/BD3-treated sputa. There were fewer 16SrRNA gene bands resulting from NaOH-treated sputum suggesting a reduction in the diversity of bacterial species. In addition, minor differences in band intensities were noted with DNA purification utilizing NPI following NaOH treatment. It appears that DNA was degraded in the denaturing conditions associated with NaOH treatment and subsequent storage in PBS or the conditions for DNA purification were not ideal.

Example 5: Live *M. tuberculosis* Recovered from Sputum Treated with STC for Up to One Week Sputum transport chemistry (STC) compositions have been found to be successful in liquefying sputum, decontaminating background flora and stabilizing total nucleic acid in the specimen, without killing *Mycobacteria* present in the specimen. These beneficial properties of the present STC composition and method provide flexibility to testing laboratories. Specimens treated with STC compositions can be collected in remote regions, transported inexpensively to a laboratory under ambient conditions, and still be successfully and accurately evaluated by the currently accepted methodologies for raw sputum analysis, including culture, smear microscopy and molecular diagnostic assays. This example provides a demonstration of the time window in which *Mycobacteria* remain viable in the STC composition at room temperature.

Experimental Methods

Treatment of Sputum from Cystic Fibrosis Patients

Raw clinical sputum samples from Cystic Fibrosis (CF) patients (kindly provided by Dr. M Desjardins, The Ottawa Hospital, Ontario, Canada) were held at 4° C. for up to 1 week. Sputa (3 mL each) were spiked with $3.3 \times 10^6$ colony forming units (cfu) of a clinical strain of virulent *M. tuberculosis* (isolated from a confirmed-positive TB patient). Spiked sputum was mixed with an equal volume of BD2 buffer, inverted 5-10 times and left at room temperature in a biosafety cabinet up to 7 days. After 24 hours and 7 days at room temperature, samples were vortexed for 10 seconds and centrifuged at 3,000×g for 15 minutes to sediment the bacterial pellet. The supernatant was poured off and the pellet was resuspended in sterile water. Aliquots were inoculated into multiple MGIT culture tubes (with PANTA/Growth Supplement) and grown at 35° C. up to 23 days.

Results and Conclusions

TB-spiked sputum held for 24 hours in BD2 buffer prior to inoculation into MGIT tubes showed positive TB growth within 7 days and there was no evidence of contamination of these cultures by background flora. TB-spiked sputum held for 7 days in BD2 buffer prior to inoculation into MGIT tubes showed positive TB growth within 21-23 days and there was no evidence of contamination by background flora. The results demonstrate that treatment of clinical sputum samples with BD2 buffer was highly effective at eliminating growth of background flora, while maintaining the viability of virulent *M. tuberculosis* following storage of the STC-treated samples for up to one week. The increased time to positive culture result of samples exposed to BD2 buffer for one week, suggested that some mycobacteria were killed and/or growth was inhibited by the longer term storage at room temperature in the STC composition. Nonetheless, the sample did retain sufficient viable mycobacteria to provide a positive culture test even after long-term storage.

Example 6: Sample Transport Chemistry Method Compared to Standard of Care Method for Molecular Detection of *Mycobacterium Tuberculosis*

The CDC recommends that clinical specimens be analyzed simultaneously by culture, acid-fast *bacillus* (AFB) staining, and nucleic acid amplification protocols (CDC, 2009). Culture is the "gold standard" for final determination of TB positivity, but it is slow and can take up to 8 weeks. Staining for AFB is rapid, but has a low sensitivity and low specificity, since it does not distinguish non-tuberculosis mycobacteria (NTM) from members of the *M. tuberculosis* complex (MTBC). Thus, rapid identification, which is essential to control spread of disease, relies on nucleic acid amplification protocols, such as real-time PCR (qPCR) and sequencing.

The assessment of antibiotic resistance in *M. tuberculosis*-infected patients is critically important to patient management and controlling the spread of disease. Standard methods for drug susceptibility testing (DST) of *M. tuberculosis* can take weeks to months to provide results. Due to the emergence of multidrug-resistant tuberculosis (MDR-TB) and extensively drug-resistant tuberculosis (XDR-TB), rapid molecular approaches have been developed. Mutations within rpoB gene are associated with rifampin (RIF) resistance, while mutations within inhA gene are associated with Isoniazid resistance. Halse et al. (2010) developed a two-step molecular approach that utilized antibiotic resistance gene pyrosequencing analysis directly with clinical specimens positive for MTBC by real-time PCR.

In this example, an independent public health diagnostics laboratory, Wadsworth Center Mycobacteriology Laboratory, was engaged to compare side-by-side the clinical evaluation of TB-positive sputum samples (kindly donated by Foundation for Innovative Diagnostics (FIND) Tuberculosis Specimen Bank) treated by two distinct methods. Specifically, 1) the "Standard of Care" method, consisting of sodium hydroxide treatment followed by bead beating, and 2) the present method, were compared in terms of sensitivity in a CLIA/CLEP-approved rtPCR assay (targeting the RD4 *Mycobacterium tuberculosis* complex (MTBC) region of difference (RD)) (Halse et al., 2011) and antibiotic resistance gene pyrosequencing assay (Halse et al., 2010). In the present method, TB-positive sputum samples were treated with an STC composition to facilitate liquefaction and chemical lysis of cells in the specimen, prior to isolation of DNA and assay testing.

In contrast to the use of the STC composition, the "Standard of Care" method includes bead beating, a mechanical method, to break open bacteria in sputum samples. While mechanical bead beating can be effective at breaking open organisms, it does create dangerous aerosols in the laboratory environment. It is, therefore, highly desirable to develop an effective, non-mechanical, chemical method to safely release DNA from *Mycobacterium tuberculosis*, without negatively impacting the clinical sensitivity of the diagnostic tests.

Experimental Method

Confirmation of Viability of *Mycobacterium tuberculosis*-Positive Sputum Samples For the present example, raw sputum samples from confirmed TB-positive patients were kindly donated by the Foundation for Innovative Diagnostics (FIND) Tuberculosis Specimen Bank. Duplicate 0.5 mL aliquots were provided from 30 patient samples and stored frozen. Using culture and smear analysis, FIND categorized these samples as follows (Table 5).

TABLE 5

Categorization of TB-Positive Sputum Specimens from FIND

| FIND Category Description | DNA Genotek Description | No. of Duplicate Sputum Specimens |
|---|---|---|
| Smear negative, Culture positive | LOW | 10 |
| Smear positive 1+, Culture positive | MID | 10 |
| Smear positive, Culture positive | HIGH | 10 |

Aliquots were shipped frozen to Wadsworth Center Mycobacteriology Laboratory (New York State Department of Health, Albany, N.Y., U.S.A.), a CLIA/CLEP-approved Clinical Laboratory for further analysis. Sputum processing, DNA extraction, rtPCR assay and pyrosequencing was conducted by Wadsworth Center Mycobacteriology Laboratory. Upon arrival at Wadsworth, duplicate aliquots from 30 donors were thawed on ice; one set of aliquots was processed using the "Standard of Care" Method (Collaborator) and the second set was treated with an STC composition prior to isolation of DNA.

Treatment of TB-positive Sputum using the "Standard of Care" Method (Collaborator)
1. 0.5 mL 3.5% NaOH was added to liquefy each 0.5 mL sputum aliquot (n=30); the aliquot was vortexed to mix the NaOH.
2. The mixture was incubated at room temperature for 15 minutes.
3. The volume of the mixture was brought up to 10 mL with sterile phosphate-buffered saline (PBS).
4. The mixture was centrifuged at 5,000 rpm for 20 minutes to pellet bacteria and the supernatant was discarded.
5. The pellet was resuspended in 0.5 mL sterile PBS.
6. 300 µl of resuspended bacteria was set aside for smear and culture testing to confirm viability of *Mycobacterium* (see Table 7).
7. To lyse bacteria, 200 mg of 105-150 micron glass beads were added to the remaining 200 µl of resuspended bacteria, followed by two 1 minute cycles of and bead beating and 1 minute on ice using a Mini-BeadBeater (BioSpec Products).

Treatment of TB-positive Sputum using Sample Transport Chemistry (STC) Method
1. 0.5 mL of BD2 buffer (2% SDS, 12 0.5 mM CDTA, 250 mM LiCl, 50 mM glycine, pH 10.5) was added to each 0.5 mL sputum aliquot (n=30), which was then vortexed to mix.
2. Proteinase K (400 µg) was added and the mixture was incubated at 50° C. in a water bath for 2 hours.
3. 400 µl of the mixture was transferred to a fresh tube and 3M potassium acetate (pH 5.5) was added to a final concentration of 150 mM.
4. The mixture was incubated on ice for 10 minutes and then centrifuged at 13,000 rpm for 5 minutes.
5. The supernatant was transferred to a clean, labeled tube and the pellet was discarded.
6. Two volumes of room temperature 95% ethanol were added to the collected supernatant and the tube was inverted 20 times to mix.
7. The samples were incubated at room temperature for 15 minutes to precipitate DNA and then centrifuged at 15,000 rpm for 2 minutes to pellet DNA.
8. The supernatant was gently removed taking care not to disturb the pellet.
9. The pellet was dissolved in 200 µL TE, vortexed briefly to fully resuspend DNA, and allowed to stand at room temperature for a minimum of 30 minutes.

Real-Time PCR for *M. tuberculosis* and Pyrosequencing for Antibiotic Resistance Duplicate reactions of 5 µL 'neat' DNA and 5 µL diluted (1:10) DNA from each purified sputum sample (above) were amplified on an ABI 7500 real-time PCR instrument using a CLIA/CLEP-approved real-time PCR assay targeting the RD4 *Mycobacterium tuberculosis* complex (MTBC) region of difference (RD) (Halse et al., 2011). Threshold cycle (CO values less than 37 were reported as positive, and samples with values greater than 37 were retested; if the results were the same, the result was reported as negative, and if they were not, they were reported as inconclusive.

Antibiotic resistance profiling was done using the previously published pyrosequencing method for rifampcin resistance (rpoB) (Halse et al, 2010) and an additional target for isonazid resistance (inhA). DNA obtained from both methods was used in separate PCR reactions to amplify specific regions of the rpoB and inhA genes. Mutations in these regions indicate probable resistance to either rifampcin and/or isonazid antibiotics.

Results and Discussion

Today, the standard of care method involves liquefaction of sputum with sodium hydroxide, followed by isolation of DNA from bacteria using mechanical bead beating. The chemical method employed in the present example is completely different in that the BD2 buffer (an STC composition) functions to liquefy sputum and lyse less robust bacteria in one step. Importantly, the present composition and method appeared to be just as effective, if not more effective, compared to the standard of care methodology, in leading to the subsequent detection of *M. tuberculosis*-specific DNA and antibiotic resistance markers.

Compared to the conventional method ("Collaborator" in Table 6 and FIG. 4), the present "STC" method led to increased sensitivity of *M. tuberculosis*-specific detection by real-time PCR in duplicate sputum samples categorized previously as 'low' and 'mid' TB-positive by culture and smear microscopy. In this example, not until DNA extracted using the "Standard of Care" method was diluted 10-fold was *M. tuberculosis* detected in 'mid' and 'high' TB-positive sputum samples (Table 6 and FIG. 4); whereas 87% of 'low' TB-burden sputum samples were detected as positive following DNA isolation utilizing the "STC" method (Table 2). Only 25% of 'low' TB-burden sputum samples were detected as positive by real-time PCR following DNA isolation using the standard of care methodology (Table 6).

Figure 4:
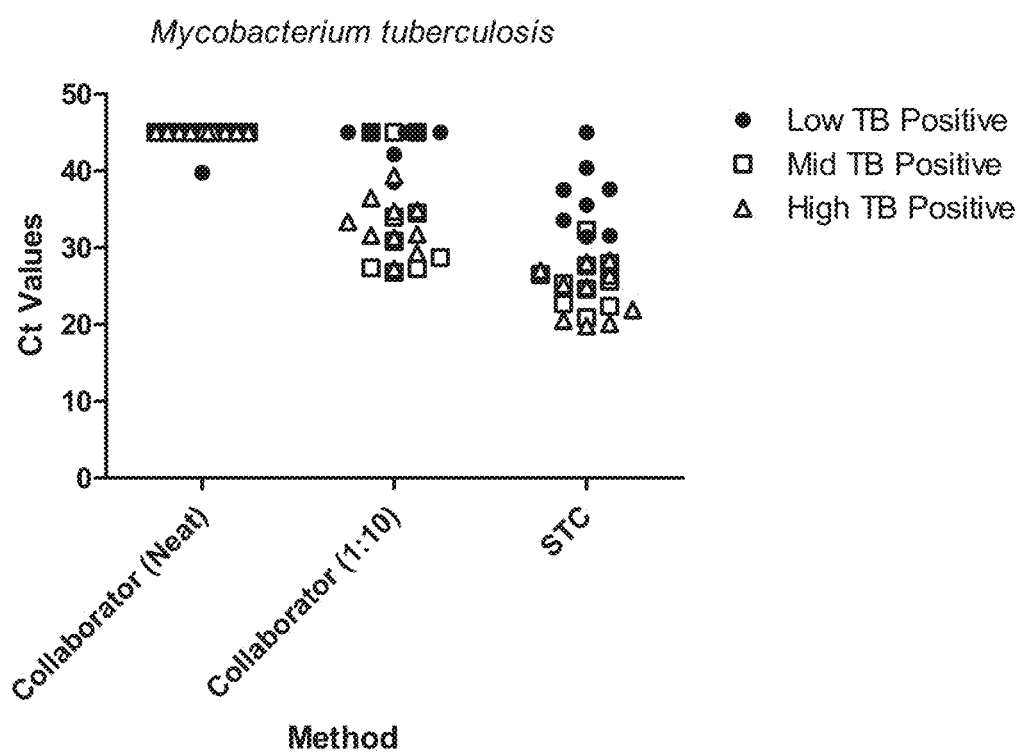
FIG. 4 graphically depicts the results from real-time PCR analysis of low, mid and high TB burdened sputum samples.

FIG. 4 illustrates the significantly improved limit of detection (lower $C_t$ values by rtPCR) of *M. tuberculosis* in all TB-positive sputum samples treated using the STC method, compared to the standard of care method (Collaborator, 1:10). For example, the $C_t$ values for 'low' TB-positive sputum ranged from 31.4-45.0 for the "STC" method, compared to 38.5-45.0 for "Collaborator" method; the $C_t$ values for 'mid' TB-positive sputum ranged from 20.9-32.3 for the "STC" method, compared to 26.8-45.0 for "Collaborator" method; the $C_t$ values for 'high' TB-positive sputum ranged from 19.8-28.3 for the "STC" method, compared to 27.2-39.3 for "Collaborator" method. The $C_t$ values are consistently lower, for all TB burden levels, when sputum was treated with STC and DNA extracted using the present method. This lower limit of detection helps ensure an accurate diagnosis of *M. tuberculosis* from patient sputum samples.

Similarly, the present composition and method is compatible with industry standard testing to predict antibiotic resistance in *Mycobacterium tuberculosis*-positive specimens. Pyrosequencing assay results obtained with the standard of care method and STC method were 100% concordant for the 6 clinical TB-positive sputum specimens tested. Importantly, from these 6 patient sputum specimens, the present STC method, but not the standard of care method, detected 2 patients (FIND 01 01 2072 and FIND 01 01 2137) with antibiotic resistance markers (inhA and rpoB genes) (Table 7). Even the gold standard culture test failed to show growth of *Mycobacteria* in these 2 patients' samples after 52 days.

The impact of the increased recovery of *Mycobacteria* DNA at the time of testing is best highlighted with the pyrosequencing data. The samples treated with the STC composition had DNA available in sufficient quantities to be tested for antibiotic resistance markers on Day 0 of testing. In contrast, the standard of care method required an average of 14 days for MGIT cultures to become positive before pyrosequencing could be repeated on samples that were negative by PCR at Day 0. The antibiotic profile of a patient is critical for case management and earlier intervention with the appropriate antibiotic therapy will decrease transmission rates and increase the patients' chances of recovery. Hence, the present invention is valuable for rapid, same-day identification of MTBC by real-time PCR and sensitive enough to detect antibiotic resistance markers for *M. tuberculosis*, without waiting for the detection of *Mycobacteria* by culture.

TABLE 6

Percentage of Sputum Samples Detected as TB-Positive by Real-time PCR Following DNA Extraction using 2 Different Methods

| Method | % Detected LOW* (n = 8) | % Detected MID (n = 10) | % Detected HIGH (n = 10) |
|---|---|---|---|
| Collaborator (neat) | 12% | 0% | 0% |
| Collaborator (1:10) | 25% | 70% | 100% |
| STC | 87% | 100% | 100% |

*2 data points excluded from low samples - TB was not detected following any extraction method or by culture

TABLE 7

Pyrosequencing Results for Two Antibiotic Resistance Markers in *M. tuberculosis*.

| Study ID # | Method | Real-time PCR C$_t$ value (in duplicate) | rpoB gene | inhA gene | MGIT Growth |
|---|---|---|---|---|---|
| FIND 01 01 2072 LOW | Collaborator | Negative (straight, 1:10) | Failed | Failed | NG |
| | STC | 31/31 | WT | C(−15)T | |
| FIND 01 01 2137 LOW | Collaborator | 34/34 (1:10) | Failed | WT | NG |
| | STC | 34/32 | Asp516Val | WT | |
| FIND 01 01 2166 MID | Collaborator | 26/26 (1:10) | Failed/WT(M) | WT | Yes (12 d) |
| | STC | 24/24 | WT | WT | |
| FIND 01 01 2287 MID | Collaborator | 34/34 (1:10) | Failed | G(−17)T | NG |
| | STC | 32/32 | Failed | G(−17)T | |
| FIND 10 01 0041 HIGH | Collaborator | 27/27 (1:10) | Failed/WT(M) | C(−15)T | Yes (10 d) |
| | STC | 20/20 | WT | C(−15)T | |
| FIND 10 01 0042 HIGH | Collaborator | 31/31 (1:10) | Failed/WT(M) | Failed/WT(M) | Yes (19 d) |
| | STC | 24/24 | WT | WT | |

WT, Wild type;
NG, No Growth;
STC, Sample Transport Chemistry
M, Pyrosequencing was done from a heat killed MGIT culture

TABLE 8

Categorization of TB-Positive Sputum Specimens from FIND

| FIND Category Description | Characterisation with STC treatment | No. of Duplicate Sputum Samples |
|---|---|---|
| Smear positive, Culture positive (SS+) | HIGH | 5 |
| Smear positive 1+, Culture positive (Smear1+ C+) | MID | 10 |
| Smear negative, Culture positive (S− C+) | LOW | 10 |

Aliquots were shipped frozen to National Jewish Health (Denver, Colo., US) for processing and testing for TB on the Example 7: Compatibility of Sample Transport Chemistry in Tuberculosis Diagnosis Using the Cepheid GeneXpert® MTB/RIF Assay Presently, a leading molecular diagnostic test for *M. tuberculosis* in sputum specimens is the Cepheid GeneXpert MTB/RIF assay, a nested, real-time PCR-based detection of *M. tuberculosis* complex DNA and rifampin resistance. In this example, the compatibility of STC composition-treated sputum with the Cepheid GeneXpert MTB/RIF assay was evaluated, compared to non-treated sputum from the same patients. Duplicate TB-positive sputum samples from 25 patients were kindly donated by the Tuberculosis Specimen Bank at Foundation for Innovative Diagnostics (FIND). An independent diagnostics laboratory, National Jewish Health (NJH), was engaged to determine the diagnostic efficacy of STC composition-treated, compared to non-treated, sputum in the Cepheid GeneXpert assay.

Experimental Method

Preparation of Raw Sputum Specimens for the GeneXpert MTB/RIF Assay

The present example utilized duplicate 0.5-1.0 mL aliquots of raw frozen sputum (donated by FIND) from 25 tuberculosis-positive patients. Culture and smear microscopy was used by FIND to confirm and categorize these samples as follows (see Table 8):

Cepheid system. Upon arrival at NJH Mycobacteriology Laboratory, duplicate aliquots from 25 donors were thawed on ice. One set of aliquots was treated with 2 volumes of Cepheid Sample Reagent (SR) Buffer and the second set was treated with an equal volume of an STC composition (2% SDS, 12 0.5 mM CDTA, 250 mM LiCl, 50 mM glycine, pH 10.5) to liquefy the specimens.

Following the addition of Cepheid SR Buffer, each aliquot was treated as follows:
 a. Mixtures were vortexed for 10-15 seconds and allowed to stand for 5 minutes at room temperature.
 b. The mixtures were vortexed for another 10-15 seconds and allowed to stand for 10 minutes at room temperature
 c. Each sample was loaded into a Cepheid GeneXpert MTB/RIF cartridge
 d. The test was performed according to Cepheid GeneXpert® MTB/RIF Assay (Protocol H.2).

Following the addition of STC, each aliquot was treated as follows:
 a. Mixtures were vortexed for 10-15 seconds and allowed to stand for 15 minutes at room temperature.
 b. The mixtures were vortexed well to mix and then centrifuged at 3000×g for 20 minutes.

c. The supernatant was carefully poured off.
d. The pellet was resuspended in 1 mL Xpert MTB/RIF SR buffer and vortexed for at least 10 seconds.
e. The mixture was incubated for 10 minutes at room temperature and vortex for at least 10 seconds.
f. The sample was incubated at room temperature for an additional 5 minutes.
g. Each 1 mL sample was loaded directly into Cepheid GeneXpert MTB/RIF cartridge.
h. The test was performed according to Cepheid GeneXpert® MTB/RIF Assay (Protocol H.2)

GeneXpert real-time PCR provides 2 results: 1) *M. tuberculosis* Positive/Negative, and 2) rifampin (RIF) antibiotic Sensitivity or Resistance (Sens/Res) (Table 9).

TABLE 9

Cepheid GeneXpert MTB/RIF Assay Results

| Level of MTB by Smear/ Culture | # of samples tested | Method | MTB Result | Correlation | Notes | Rifampin Result | Correlation | Notes |
| --- | --- | --- | --- | --- | --- | --- | --- | --- |
| High | 5 | STC | 5/5 Positive; | 100% | | 2/5 Res; | 100% | |
| | | NJH | 5/5 Positive | | | 2/5 Res | | |
| Mid | 10 | STC | 8/8 Positive; | 100%$^{a,b}$ | | 0/9 Res; | 100% | |
| | | NJH | 8/8 Positive | | | 0/9 Res | | |
| Low | 10 | STC | 8/9 Positive; | 88%$^{a,c}$ | 1 discrepant call: STC = No MTB detected; NJH = MTB detected | 2/8 Res; | 88-100%$^{d}$ | 1 discrepant call: STC = Res; NJH = Sens |
| | | NJH | 9/9 Positive | | | 1/8 Res | | |

$^{a}$One sample was no MTB detected by both methods; excluded from calculations.
$^{b}$One sample failed due to "Post Run Analysis Error"; excluded from calculations.
$^{c}$Biological variation in aliquots may have played a role; additional work may be undertaken to resolve discrepancy.
$^{d}$88% if call was incorrect; 100% if call was correct; additional work may be undertaken to resolve discrepancy.

Results and Conclusions

Sediments extracted from STC composition-treated sputum were fully compatible with the Cepheid GeneXpert® MTB/RIF Assay system. Specimens classified as smear positive/culture positive (both High and Mid) and treated with STC were 100% concordant for *M. tuberculosis* and RIF resistance by the Cepheid molecular assay, compared to untreated sputum from the same patients (Table 9).

For smear negative/culture positive (Low) specimens, there was 88% concordance between STC composition-treated and untreated sputum samples in the detection of *M. tuberculosis* by real-time PCR (Table 9). Specifically, one donor's sample treated with STC gave a negative result for *M. tuberculosis*. Biological variation between different aliquots from the same patient may have played a role in this instance, making MTB undetectable in this "Low" specimen.

When evaluating RIF resistance, there was one discrepant call for smear negative/culture positive (Low) specimens. Two donors were identified as RIF-resistant using STC composition-treated sputum; while 1 donor was identified as resistant when untreated sputum was processed using the Cepheid SR buffer method (Protocol H.2). This discrepancy could be explained by an increase in sensitivity of the assay when sputum was pre-treated with the STC composition prior to analysis.

Example 8: Spores of *Bacillus Anthracis* Survive Sample Transport Chemistry

Anthrax is an acute, often lethal, disease caused by the rod-shaped, gram-positive, aerobic bacterium *Bacillus anthracis* that normally rests in endospore form in the soil. Like *Clostridium difficile*, *B. anthracis* can form dormant endospores, which are very hard to eradicate, surviving harsh conditions for decades or even centuries. Anthrax does not spread directly from one infected animal or person to another, it is spread by spores. When spores are inhaled or ingested, or come into contact with a skin lesion on a host, they may become reactivated and multiply rapidly. The hardiness of anthrax spores, and their ease of production in vitro, makes them extraordinarily well suited to use (in powdered and aerosol form) as biological weapons.

While previous examples demonstrated that *Mycobacterium tuberculosis* remained viable in the present composition, the present example demonstrates that other hardy microorganisms, such as *Bacillus anthracis* spores, remain viable after treatment with an STC composition.

Experimental Method

Work was conducted at the New York State Department of Health, Wadsworth Center, Biodefense Laboratory, USA.

Preparation of *B. anthracis* Spores

Frozen stock culture of *B. anthracis* Sterne Strain was cultured on Trypticase Soy Agar with 5% Sheep's Blood and incubated at 35° C. with 5% $CO_2$ for 24 hours. After initial incubation, this culture was transferred to multiple (minimum of 10) *Bacillus* Sporulation Agar plates and incubated aerobically at 35° C. with $CO_2$ for up to 2 weeks.

Malachite Green spore staining was performed every 3 to 4 days to monitor sporulation of *B. anthracis* in vitro. When the malachite green stains prepared showed almost complete sporulation of organisms, the spores were harvested into 5.0 mL of PBS (pH 7.4) and stored at room temperature until use.

Determination of Spore Concentration

*B. anthracis* spore suspension was diluted to $10^{-3}$ in PBS. An aliquot (10 μL) of this final dilution was loaded into each clean well of a 2-chamber hemocytometer slide. Hemocytometer chambers were observed at 40× magnification without oil for spore counting. Spores were visualized as round or oval black cells on the light field grid of the hemocytometer.

Treatment of Spores 1. 7004 of spore stock suspension was prepared, at the required concentration.
2. Each sample was split into 2×3504 volumes; with one 3504 aliquot used as untreated or "control":
   a. 504 aliquot was removed to confirm spores were viable by plating onto Trypticase Soy Agar with 5% Sheep's Blood (see below).
4. The second 3504 aliquot was used for STC Method:
   a. 3504 BD2 buffer (2% SDS, 12 0.5 mM CDTA, 250 mM LiCl, 50 mM glycine, pH 10.5) was added to the 350 μL spore stock suspension of *B. anthracis*; and vortexed to mix.
   c. The mixture was incubated at room temperature for 15 minutes, and then 1004 was removed for culture ("STC") and plated onto Trypticase Soy Agar with 5% Sheep's Blood (see below).

Culture of Spores to Determine Viability

*B. anthracis* aliquots were plated directly onto Trypticase Soy Agar with 5% Sheep's Blood and incubated at 35° C. with 5% $CO_2$. After 24 hours, colony-forming units (CFU) were recorded.

Results and Discussion

Figure 5:
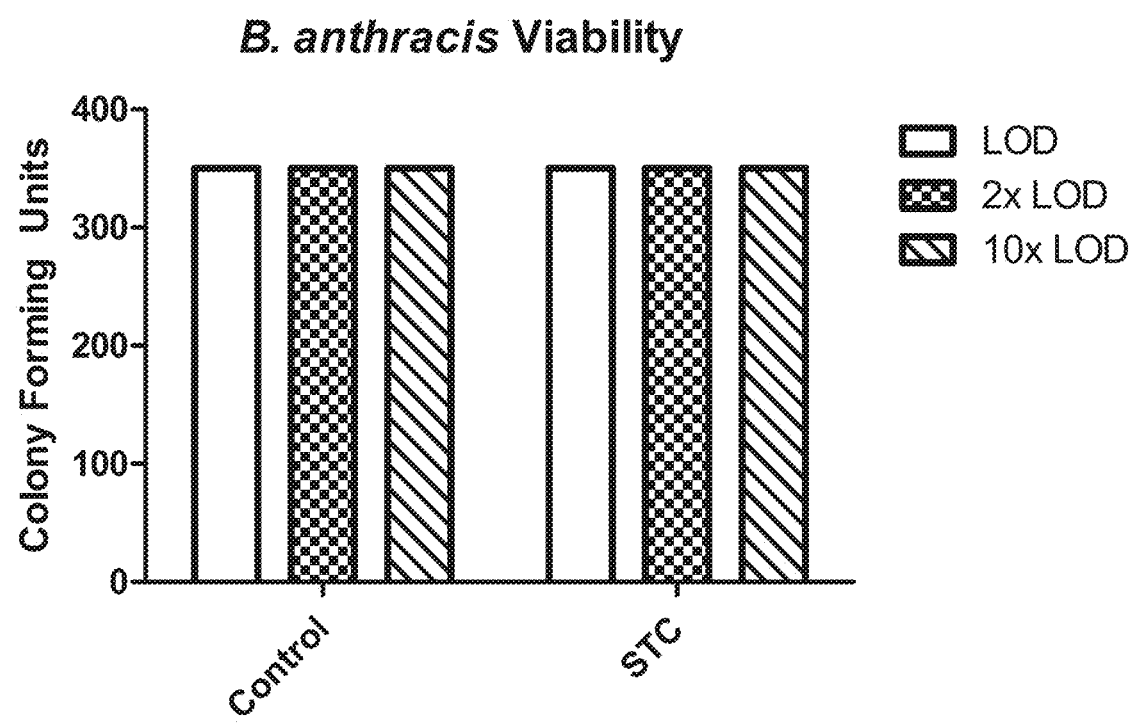

This example demonstrated that *B. anthracis* spores were not killed with STC treatment (FIG. 5). Both untreated and STC-treated spores produced equivalent numbers of vegetative bacteria following 24 hours under favourable culture conditions.

Example 9: *Mycobacterium* is Viable in Sample Transport Chemistry for a Week at Ambient Temperatures Ambient temperature can vary widely from region to region with fluctuations throughout the day. During collection and transport to the laboratory, biological samples are exposed to this broad range of temperatures unless measures are taken. In developing countries, due to high cost and lack of infrastructure, samples are transported to the laboratory at ambient temperature, compromising the quality of the sample and validity of the test results.

In example 1, attenuated *Mycobacterium tuberculosis* H37Ra (aMTB) spiked into sputum remained viable in the present composition, STC, at room temperature (20-25° C.) and 4° C. up to 30 days. In the present example, aMTB, in the absence of mucoid sputum, was in direct contact with STC or PBS and exposed to temperatures ranging from 4° C. to 40° C. for 1, 2, 3, 4 and 7 days. Following up to 7 days exposure to STC, the *Mycobacteria* were cultured to assess viability; time to positive culture result was monitored. As control, this experiment was repeated with *E. coli*, a less hardy microorganism than *Mycobacteria*.

Experimental Method

Treatment of Attenuated *Mycobacterium tuberculosis* and *E. coli* with STC or PBS A. aMTB ($2 \times 10^6$ CFU/mL) and *E. coli* ($2 \times 10^6$ CFU/mL) were spiked into 10 mL of STC (2% SDS, 12.5 mM CDTA, 250 mM LiCl, 50 mM glycine, pH 10.5) or phosphate buffered saline (PBS) in multiple 50 mL sterilized tubes.

B. Held each tube at the appropriate temperature (4° C., room temperature (20-25° C.), or 40° C.) for the allotted time (1, 2, 3, 4, or 7 days).
C. Removed 3 mL of spiked microorganism in STC or PBS from each tube.
D. Centrifuged at 3500 rcf for 20 minutes to pellet intact bacteria.
E. Discarded the supernatant and resuspended the pellet in 0.5 mL sterile PBS
F. Inoculated 100 μL of resuspended bacteria into 5×5 mL supplemented M7H9 broth.
G. Incubated at 37° C. and checked for growth daily.
H. Culture control:
   a. Inoculated aMTB ($10^6$ CFU/mL) from stock into 5 mL M7H9 broth each day a test sample was cultured.
   b. Inoculated *E. coli* ($10^6$ CFU/mL) from stock into 5 mL M7H9 broth each day a test sample was cultured.
   c. Incubated control cultures at 37° C. with test samples.
I. Recorded the number of days until positive for all samples
J. For aMTB, continued incubating until 0.5 McFarland Standard turbidity was reached.
K. For *E. coli*, continued incubating until 1.0 McFarland Standard turbidity was reached.

Extraction of DNA from aMTB Treated in STC or PBS for 30 Days at 4° C. and 40° C.

A. Transferred 200 μL of aMTB (treated with PBS for 30 days at 4° C. and 40° C.) to a fresh tube and mixed with 200 μL of BD2 buffer.
B. Transferred 200 μL of aMTB (treated with STC for 30 days at 4° C. and 40° C.) to a fresh tube for DNA extraction.
C. Sodium (meta)periodate was added to each tube to a final concentration of 30 mM and vortexed to mix.
D. The mixtures were incubated at 70° C. in a water bath for 20 minutes.
E. Samples were cooled at room temperature for 2 minutes.
F. 1M Tris buffer (pH 7) was added to a final concentration of 50 mM.
G. The mixtures were incubated at room temperature for 10 minutes.
H. 3M potassium acetate (pH 5.5) was added to a final concentration of 150 mM, vortexed to mix.
I. Mixtures were incubated on ice for 10 minutes and then centrifuged at 13,000 rpm for 5 minutes.
J. Supernatant was transferred to a clean, labelled tube and the pellet was discarded.
K. Two volumes of room temperature 95% ethanol was added to the supernatant in the tube and the tube was inverted 20 times to mix.
L. The mixture was incubated at room temperature for 10 minutes to precipitate DNA and then centrifuged at 15,000 rpm for 2 minutes to pellet DNA.
M. The supernatant was gently removed and discarded taking care not to disturb the pellet.

The pellet was dissolved in 200 μL TE.

rtPCR Conditions

DNA isolated from aMTB treated 30 days with STC or PBS at 4° C. and 40° C. was subjected to qPCR specific for *Mycobacterium*, the RD4 Taqman Real-time PCR assay (same protocol as example 1).

Results and Discussion aMTB is viable in the present composition, STC, for 7 days over a broad range of temperatures (4-40° C.), typical of transport conditions. Positive aMTB cultures show 0.5 McFarland turbidity growth within the standard 42 days incubation at 35° C. (Table 10). aMTB, exposed to STC, loses some viability as it is held at 4° C., room temperature and 40° C. up to 7 days, as shown by the longer times periods to achieve 0.5 McFarland turbidity growth (Table 10), compared to aMTB exposed to PBS. Interestingly, aMTB in PBS also showed some loss of viability when held at 40° C. for even 1 day, suggesting that temperature has significant impact on aMTB viability.

In contrast, there was complete loss of viability of *E. coli* in STC in all temperatures tested by day 1 (Table 11). There was no loss of viability of *E. coli* in PBS at 4° C., room temperature and 40° C. up to 7 days. Hence, STC will keep aMTB viable for at least 7 days ranging from 4-40° C., while at the same time, eliminate bacteria like *E. coli* on contact, thereby reducing background flora of a biological sample.

Importantly, qPCR (Table 12), specific for MTB DNA, shows that the quantity of aMTB remained constant in STC for 30 days at 4° C. and 40° C. Similar values were obtained for aMTB treated with PBS at these extreme temperatures for 30 days (Table 12). Hence, this example shows that aMTB is stable in STC, i.e. it doesn't proliferate or degrade over a wide range of temperatures for at least one month; insuring samples that reach distant laboratories closely represent the state of the patient in vivo.

TABLE 12 qPCR of DNA extracted from STC- and PBS-treated aMTB after 30 days.

| qPCR Replicate | Stock 4° C. | PBS-treated aMTB | | STC-treated aMTB | |
|---|---|---|---|---|---|
| | | 4° C. | 40° C. | 4° C. | 40° C. |
| 1 | 20.44 | 21.29 | 21.73 | 21.65 | 22.73 |
| 2 | 21.01 | 22.02 | 21.66 | 20.71 | 20.47 |
| 3 | 20.91 | 23.62 | 20.89 | 20.96 | 21.09 |

Example 10: Effect of Buffer Composition on the Viability of and DNA Extraction from *Mycobacterium tuberculosis*

As seen in Example 5, *M. tuberculosis* remains viable in an STC composition BD2 for 7 days at room temperature. The fundamental components of the STC compositions may be varied or "tailored" for specific sample types and uses. The relationship between chelating agents, detergents, pH and buffering agents were investigated for their effect on both the viability of attenuated *M. tuberculosis*, as well as the subsequent recovery of high molecular weight (HMW) DNA.

In this example, the following STC compositions were tested:

TABLE 10

Viability of aMTB in STC from 4° C. to 40° C.

| Organism | Chemistry | Hold Temperature (° C.) | Time to Positive Culture (Days to 0.5 McFarland) of aMTB | | | | |
|---|---|---|---|---|---|---|---|
| | | | 1 Day in STC | 2 Days in STC | 3 Days in STC | 4 Days in STC | 7 Days in STC |
| aMTB | STC | 4 | 21 | 23 | 23 | 24 | 28 |
| | | 22 | 21 | 23 | 23 | 24 | 28 |
| | | 40 | 17 | 16 | 23 | 28 | 38 |
| | PBS | 4 | 13 | 16 | 15 | 14 | 18 |
| | | 22 | 13 | 16 | 15 | 19 | 32 |
| | | 40 | 24 | 23 | 29 | 28 | 32 |
| aMTB stock | PBS | 4 | 13 | 16 | 15 | 14 | 18 |

TABLE 11

Viability of *E. coli* in STC from 4° C. to 40° C.

| Organism | Chemistry | Hold Temperature (° C.) | Time to Positive Culture (Days to 1.0 McFarland) of *E. coli* | | | | |
|---|---|---|---|---|---|---|---|
| | | | 1 Day in STC | 2 Days in STC | 3 Days in STC | 4 Days in STC | 7 Days in STC |
| *E. coli* | STC | 4 | NG | NG | NG | NG | NG |
| | | 22 | NG | NG | NG | NG | NG |
| | | 40 | NG | NG | NG | NG | NG |
| | PBS | 4 | 1 | 1 | 1 | 1 | 1 |
| | | 22 | 1 | 1 | 1 | 1 | 1 |
| | | 40 | 1 | 1 | 1 | 1 | 1 |
| *E. coli* stock | PBS | 4 | 1 | 1 | 1 | *3 | 1 |

Note:
*culture checked after weekend; this culture likely reached 1.0 McFarland in 1 day
NG, No growth

TABLE 13

Compositions tested in this example

| Chemistry | Salt | Chelating Agent | Detergent | Buffering Agent | pH |
|---|---|---|---|---|---|
| BD2 | 250 mM LiCl | 12.5 mM CDTA | 2% SDS | 50 mM Glycine | 10.5 |
| Variant #1 | 250 mM LiCl | 12.5 mM EDTA | 2% SDS | 50 mM Glycine | 10.5 |
| Variant #2 | 250 mM LiCl | 12.5 mM EDTA | 2% Triton X-100 | 50 mM Borate | 9.3 |
| BD4 | 250 mM LiCl | 12.5 mM CDTA | 2% SDS | 50 mM Borate | 9.3 |

Experimental Methods:
Plated Colonies and DNA Extraction
Saliva samples were collected from healthy individuals and treated as follows:
1. 0.4 mL of saliva or water (control for DNA extraction) was mixed with 0.5 mL of the above chemistries (Table 13) and tubes were incubated 30 minutes to allow liquefaction.
2. 100 μL of a suspension of attenuated *M. tuberculosis* cells (strain h37a; aMTB) washed in PBS were added per sample (one tube per chemistry). Alternatively, 100 μL of sterile water was added to saliva in chemistries to create un-spiked control samples.
3. Samples were mixed by vortexing and incubated for 30 minutes, 2, 4 and 8 days at room temperature when samples were serially diluted and spread-plated on Middlebrook agar plates (see below for details). Colonies on plates were enumerated manually after incubation at 35° C. for 3-4 weeks
4. At each time-point outlined in step 3, an aliquot of each sample was subjected to vortex bead-beating to extract total DNA. Briefly, 250 μL of sample was pelleted, washed in PBS and brought up in 340 μL of sterile RNase-free water. 30 μL was serially diluted and plated on Middlebrook plates, while 300 μL was added to 300 μL of BD1 (250 mM LiCl, 50 mM CDTA, 4% SDS, pH 6.8) in a screw-capped 2-mL tube containing 250 mg of Cole High-refractive index silica beads. The BD1 sample mixture was then processed in a Bio Spec bead-beater for 1 minute.
5. Debris was removed by centrifugation for 5 minutes at 15,000 rpm in a microcentrifuge.
6. DNA was purified from samples using an abbreviated version of the method outlined in Example 1 (Extraction of DNA from aMTB-spiked BD2 Buffer-Treated Sputum using the Periodate Method; specifically, steps 8-13 were used, and step 12 used a 1 hour incubation at −20° C.).
7. Samples were centrifuged for 3 minutes at 15,000 rpm in a microcentrifuge, pellets were brought up in 504 of RNase-free water and 12 μL were analysed by agarose gel electrophoresis on a 0.8% agarose gel (see FIG. 6 below).

Results and Conclusions
Table 14 summarizes the results of the enumeration of *M. tuberculosis* colonies after the indicated incubation times. An entry of ND indicates the number of colonies was not determined due to the presence of contamination. On all other plates, *M. tuberculosis* was the only bacterium present. An entry of <$10^2$ indicates that no colonies were observed on the plate with the lowest dilution, which is the limit of detection for this method.

TABLE 14

Enumeration of viable *M. tuberculosis* per 0.6 mL human saliva after incubation in STC compositions for the indicated incubation times.

| STC | 30 Minutes | 2 Days | 4 Days | 8 Days |
|---|---|---|---|---|
| BD2 | $7.0 \times 10^5$ | $5.0 \times 10^4$ | $1.0 \times 10^3$ | <$10^2$ |
| Variant #1 | $6.8 \times 10^5$ | $5.2 \times 10^5$ | $5.0 \times 10^3$ | <$10^2$ |
| Variant #2 | $2.0 \times 10^5$ | $4.0 \times 10^4$ | <$10^2$ | <$10^2$ |
| BD4 | $1.5 \times 10^5$ | $5.0 \times 10^4$ | $5.0 \times 10^3$ | <$10^2$ |
| Water (control) | $1.0 \times 10^7$ | ND | ND | $3.0 \times 10^5$ |

Figure 6:
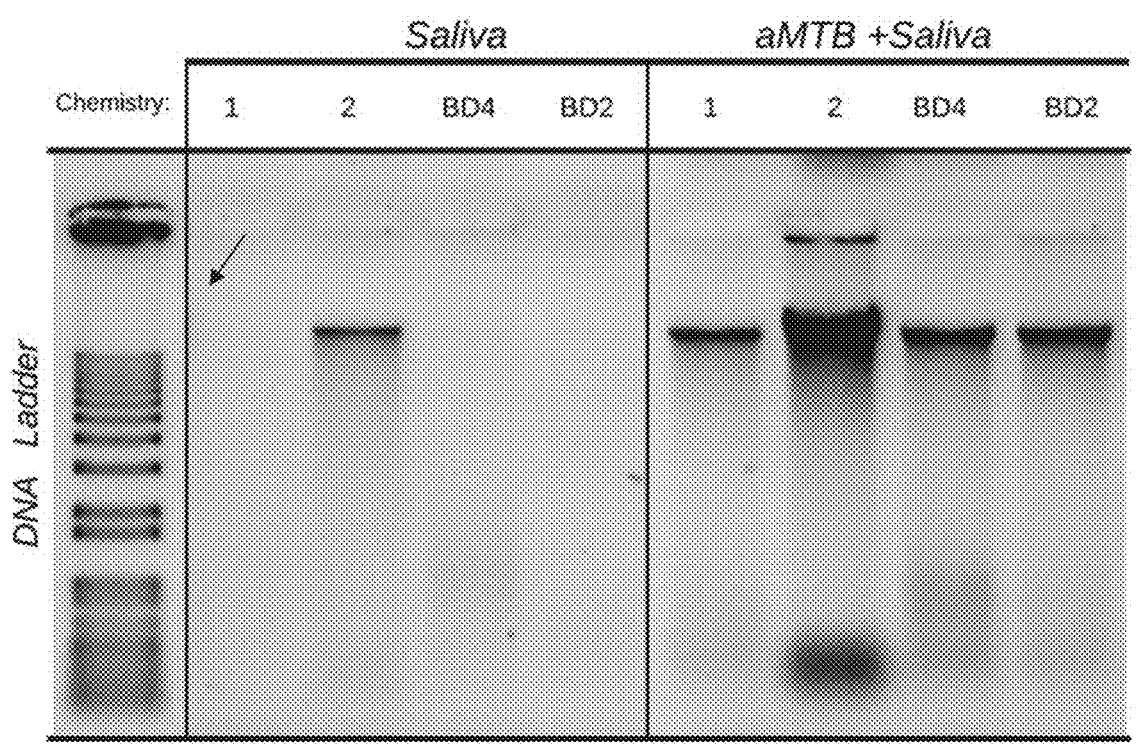
FIG. 6 is a photograph of the gel result for the t=2 days time point of the presence of *M. tuberculosis* from human saliva.

Results and Conclusions
FIG. 6 shows (as an example) the agarose gel result for the t=2 days time point. Intact high molecular weight (HMW) DNA is recovered after treatment of saliva samples with BD2 or the indicated chemistry variants. All samples containing aMTB show a marked increase in the amount of recovered DNA, demonstrating the contribution of aMTB to the total nucleic acids present. The uppermost band of the DNA ladder (arrowhead) is equal to ~23 kB. All recovered DNA bands are higher than this point, indicating the presence of HMW DNA.

In this example, the effect on extraction of DNA from and viability of attenuated *M. tuberculosis* after incubation in BD2 or the related chemistry variants mixed with saliva was investigated in order to demonstrate the fundamental utility of different combinations of the STC components. DNA extraction from *M. tuberculosis* was assessed by agarose gel electrophoresis and controls were included to distinguish between salivary DNA and Mycobacterial DNA. Intact high molecular weight (HMW) DNA from *M. tuberculosis* could be obtained at all time-points after incubation in all compositions tested, followed by bead-beating (FIG. 6).

The viability of *M. tuberculosis* was determined by enumeration of plated colonies following incubation in BD2 or related chemistries. *M. tuberculosis* is notorious for forming clumps of cells which make exact determination of viable MTB cells present in the samples difficult. Additionally, contamination was observed in samples mixed with borate-buffered chemistry containing triton X-100. Despite these difficulties, the overall trends of survival of *M. tuberculosis* in these chemistries could be determined. While there is a reduction in viability over time, *M. tuberculosis* maintains viability even after four days incubation in BD2 and related chemistries (Table 14). This is consistent with the results of Example 5, where virulent *M. tuberculosis* remained viable following storage in the STC composition for up to one week. Whereas all chemistries drastically reduced viability after 8 days, there is some variation in the impact on viability at earlier time points (compare BD2 to variant #2). In all cases, saliva samples containing MTB yielded HMW DNA at all time points tested (shown for time point t=2 days in FIG. 6). Ultimately, these data demonstrate that variations of the STC compositions perform equally well with respect to HMW DNA recovery and viability of hardy microorganisms. Presently, one of the input requirements of state of the art molecular diagnostic testing is quality, HMW DNA. This example demonstrates that the STC compositions are able to provide such DNA for subsequent molecular diagnostic testing.

Example 11: STC Compositions are Effective in Eliminating Opportunistic Pathogens Present in Sputum In many high burden TB countries, safe and efficient transport of TB positive samples is a problem. Samples are regularly discarded at the processing laboratory due to putrefaction caused by long transport times at ambient temperatures. The STC compositions are intended to preserve the viability of hardy microorganisms such as *M. tuberculosis*, while eliminating the background microflora of sputum and thereby allowing transport of sputum samples without the risk of putrefaction prior to molecular and culture TB diagnostics.

*Pseudomonas aeruginosa* and *Moraxella catarrhalis* are opportunistic pathogens capable of causing respiratory tract infections often in immune-compromised or chronically sick persons. *P. aeruginosa* is a gram negative bacterium that forms biofilms and is one of the bacteria most isolated from people with nonsocomial (hospital acquired) infections. Because of its association with people with cystic fibrosis, it is also frequently found in sputum samples. *M. catarrhalis* is a gram negative bacterium that is capable of both aerobic and anaerobic growth. It can survive for at least three weeks in expectorated sputum and is a potential contaminant of sputum samples even after NALC-NaOH treatment. Here, the ability of *P. aeruginosa* and *M. catarrhalis* to survive treatment with STC compositions is investigated.

a) The Impact of STC Compositions on Background Microorganisms in Human Sputum Samples
Materials and Methods:
1. 600 µL of pooled, certified TB-negative human sputum (from six donors, Tissue Solutions, source 53 France) was mixed with 700 µL PBS, BD2 (250 mM LiCl, 12.5 mM CDTA, 2% SDS, 50 mM glycine, pH 10.5) or BD3 (250 mM LiCl, 50 mM CDTA, 4% SDS, pH 6.8).
2. Samples were mixed and incubated at room temperature for 10 minutes, 3 hours or 24 hours when serial dilutions were prepared from each sample to determine number of viable bacteria.
3. For plating at each time-point, 100 µL aliquots were washed in PBS (exception: samples in PBS were not washed prior to plating). Serial dilutions were prepared in PBS and 100 µL aliquots of dilutions were plated on trytpic soy agar t=0 (10 mins, 0.17 hour), 3 and 24 hours post incubation. Background flora of bacteria was enumerated by counting CFUs on these plates after incubation at 35° C. (Table A).

Results:

TABLE 15

Enumeration of viable background bacteria per 0.6 mL human sputum after incubation in STC compositions for the indicated incubation times.

| Incubation Time (h) | PBS | BD3 | BD2 |
|---|---|---|---|
| 0.17 | $1.6 \times 10^7$ | $9.3 \times 10^3$ | 90 |
| 3 | $2.3 \times 10^7$ | $1.9 \times 10^3$ | <10* |
| 24 | $2.5 \times 10^7$ | 10 | <10* |

*An entry of <10 indicates that no colonies were observed on the plate with the lowest dilution ($10^1$), which is the limit of detection for this method.

b) The Impact of STC Compositions on *Pseudomonas aeruginosa* and *Moraxella catarrhalis*
Materials:
Overnight cultures of *M. catarrhalis* ATCC 25238 and *P. aeruginosa* ATCC 10145
Filter-sterilized STC compositions: BD2 (250 mM LiCl, 12.5 mM CDTA, 2% SDS, 50 mM glycine, pH 10.5); BD3 (250 mM LiCl, 50 mM CDTA, 4% SDS, pH 6.8); BD4 (250 mM LiCl, 12.5 mM CDTA, 2% SDS, 50 mM borate, pH 9.3)
sterile water, sterile Dulbecco's phosphate-buffered saline (PBS), trytpic soy broth (TSB), trytpic soy agar (TSA), brain heart infusion (BHI) broth and agar
turntable for microbiology
Experimental Methods:
Viability determined by plating
1. *M. catarrhalis* was grown in BHI broth from a plate stored at 4° C. *P. aeruginosa* was grown in TSB from a plate stored at 4° C.
2. After overnight growth at 37° C., bacteria were harvested, washed and approximately 100 cells/100 µL PBS were incubated in 1 mL of STC composition (1:1 with water) or PBS.
3. 300 µL aliquots were taken after 15 minutes, 1 hour and 24 hours.
4. At each time-point, the pellets were washed in DPB (*P. aeruginosa*) or BHI broth (*M. catarrhalis*) and serial dilutions were made in PBS (*P. aeruginosa*) or BHI broth (*M. catarrhalis*).
5. Dilutions were plated on TSA (*P. aeruginosa*) or BHI agar (*M. catarrhalis*), and plates were incubated overnight at 35° C.; colonies on plates were enumerated by manual counting (Table 16).
Viability Determined by Broth Growth
1. *M. catarrhalis* was grown in BHI broth from a plate stored at 4° C. *P. aeruginosa* was grown in TSB from a plate stored at 4° C.
2. After overnight growth at 37° C., bacteria were harvested, washed and approximately 100 cells were incubated in 1 mL of chemistry (1:1 with water) or PBS. The initial inoculum was determined by serial dilutions and enumeration on agar plates.
3. 300 µL aliquots were taken after 15 minutes and 2 hours.
4. At each time-point, intact bacteria were pelleted and washed in TSB or BHI broth.
5. The aliquots were then used to inoculate 2 mL of TSB (*P. aeruginosa*) or BHI broth (*M. catarrhalis*)
6. The broth was incubated at 37° C. with shaking, 180 rpm, overnight and any growth was recorded (Table 17).

Results:

TABLE 16

Enumeration of *P. aeruginosa* (TSA plates) and *M. catarrhalis* (BHI plates) following incubation in STC compositions for the indicated incubation times

|  | Incubation Time (h) | PBS | BD3 | BD2 | BD4 |
|---|---|---|---|---|---|
| *P. aeruginosa* | 0.25 | $9.0 \times 10^7$ | $1.1 \times 10^7$ | <100 | <100 |
|  | 1 | $7.5 \times 10^7$ | $8.5 \times 10^6$ | <100 | <100 |
|  | 24 | $1.0 \times 10^8$ | 600 | <100 | <100 |
| *M. catarrhalis* | 0.25 | $3.0 \times 10^8$ | <100 | <100 | <100 |
|  | 1 | $6.0 \times 10^8$ | <100 | <100 | <100 |

TABLE 17

Growth of *P. aeruginosa* (TSB broth) and *M. catarrhalis* (BHI broth) following incubation in STC compositions for the indicated incubation times

|  | Incubation Time (h) | PBS | BD3 | BD2 | BD4 |
|---|---|---|---|---|---|
| *P. aeruginosa* | 0.25 | ++ | ++ | -- | -- |
|  | 2 | ++ | ++ | -- | -- |
| *M. catarrhalis* | 0.25 | ++ | -- | -- | -- |
|  | 2 | ++ | -- | -- | -- |

Conclusions

While the present composition preserves the viability of hardy microorganisms such as *M. tuberculosis* for prolonged periods of time (Examples 5 and 10), it is crucial that the contamination caused by the growth of other more rapidly growing microorganisms is eliminated as soon as possible. Here, we found that the STC compositions are effective at eliminating plate growth of *P. aeruginosa* and *M. catarrhalis* between 15 minutes and 24 hours of incubation (Table 16). There is variation between compositions, with BD2 and BD4 acting more effectively against *P. aeruginosa* than BD3 (Tables 16 and 17).

As the limit of detection of the plate-counting experiment was 100 cells, it is possible that some bacteria survived treatment with the STC compositions that could lead to contamination of *Mycobacterium* broth cultures. To address this, viability after incubation in STC compositions was also investigated by broth culture. Here, any surviving bacteria should multiply leading to easily observable growth in broth. In agreement with the plating results, only cultures inoculated with cells that had been treated with PBS or *P. aeruginosa* treated with BD3 resulted in growth of bacteria after overnight incubation (Table 17). This example demonstrates that the STC compositions can quickly and effectively eliminate less hardy microorganisms, which are a potential source of contamination in biological samples such as sputum, making compositions of the present invention ideal transport solutions for TB samples.

Example 12: STC Compositions are Effective in Rapidly Eliminating Both Gram-Negative and Gram-Positive Bacterial Species, as Well as Yeast Species Hardy microorganisms such as *M. tuberculosis* can be found in a variety of environments, together with many other bacterial species, as well as other microorganisms such as yeasts. This example demonstrates the broad applicability of the STC compositions in rapidly eliminating the viability of various microorganisms. Several species of bacteria were chosen due to their presence in a range of environments such as soil (*Bacillus thuringiensis, Bacillus subtilis*), human skin (*Staphylococcus aureus*), and mammalian gastrointestinal tracts (*Yersinia enterocolitica, Candida albicans*).

Materials:
Overnight cultures
Filter-sterilized BD2 (250 mM LiCl, 12.5 mM CDTA, 2% SDS, 50 mM glycine, pH 10.5), BD3 (250 mM LiCl, 50 mM CDTA, 4% SDS, pH 6.8) and BD4 (250 mM LiCl, 12.5 mM CDTA, 2% SDS, 50 mM borate, pH 9.3)
Sterile water, sterile Dulbecco's phosphate-buffered saline (PBS), tryptic soy broth (TSB), tryptic soy agar (TSA), brain heart infusion (BHI) broth and agar, TSB and TSA supplemented with 0.1% cysteine (TSBC and TSAC respectively), YEPD plates and broth for yeast.
Turntable for microbiology
Experimental Methods:
1. Bacteria and yeast were grown in the recommended growth media and at the recommended temperature (see step #5, below for details).
2. After overnight growth cells were harvested, washed and 109 cells in 100 µL PBS were incubated in 1 mL of STC chemistries (1:1 with water) or PBS.
3. 300 µL aliquots were taken after 15 minutes, 1 hour and 24 hours.
4. At each time-point, aliquots were washed and serially diluted in media.
5. Dilutions were plated on YEPD (*C. albicans*), TSAC (*F. philomiragia*), BHI agar (*Y. enterocolitica*), or TSA (all others) and plates were incubated overnight at 30° C. (*Y. enterocolitica, C. albicans*), or 35° C. (all others) and colonies on plates enumerated by counting (Table 18).

Results:

TABLE 18

Enumeration of the indicated microorganisms following incubation in STC compositions for the indicated incubation times

| Bacterial Species | Incubation Time (h) | Medium | PBS | BD3 | BD2 | BD4 |
|---|---|---|---|---|---|---|
| *B. thuringiensis* | 0.25 | TSA | $3.2 \times 10^7$ | <100 | <100 | <100 |
|  | 1 | TSA | $8.1 \times 10^7$ | <100 | <100 | <100 |
| *Y. enterocolitica* | 0.15 | BHI | $7.5 \times 10^8$ | $4.8 \times 10^7$ | <100 | <100 |
|  | 1 | BHI | $7.9 \times 10^8$ | $4.0 \times 10^7$ | <100 | <100 |
|  | 24 | BHI | $7.8 \times 10^8$ | $2.8 \times 10^5$ | <100 | <100 |
| *F. philomiragia* | 0.15 | TSAC | $3.7 \times 10^8$ | $1.0 \times 10^8$ | <100 | Not tested |
|  | 1 | TSAC | $2.5 \times 10^8$ | $1.5 \times 10^7$ | <100 | Not tested |
|  | 24 | TSAC | $9.4 \times 10^8$ | $1.4 \times 10^5$ | <100 | Not tested |

TABLE 18-continued

Enumeration of the indicated microorganisms following incubation
in STC compositions for the indicated incubation times

| Bacterial Species | Incubation Time (h) | Medium | PBS | BD3 | BD2 | BD4 |
|---|---|---|---|---|---|---|
| S. aureus | 0.15 | TSA | $8.0 \times 10^8$ | <100 | <100 | Not tested |
|  | 1 | TSA | $6.4 \times 10^8$ | <100 | <100 | Not tested |
| B. subtilis | 0.15 | TSA | $1.1 \times 10^8$ | <100 | <100 | Not tested |
|  | 1 | TSA | $4.7 \times 10^7$ | <100 | <100 | Not tested |
| K. pneumonia | 0.15 | TSA | $3.5 \times 10^8$ | $5.7 \times 10^7$ | <100 | Not tested |
|  | 1 | TSA | $2.8 \times 10^8$ | $2.9 \times 10^7$ | <100 | Not tested |
|  | 24 | TSA | $1.6 \times 10^7$ | $2.6 \times 10^6$ | <100 | Not tested |
| C. albicans | 0.15 | YEPD | $1.7 \times 10^7$ | <100 | <100 | Not tested |
|  | 1 | YEPD | $1.7 \times 10^7$ | <100 | <100 | Not tested |

Conclusions

The effect of incubating both gram-positive (*B. thuringiensis*, *S. aureus*, *B. subtilis*) and gram-negative (*Y. enterocolitica*, *F. philomiragia*, *K. pneumonia*) bacteria and yeast (*C. albicans*) in STC compositions was investigated. There was a marked difference in effect of BD3 on the bacterial species tested; while gram-positives and *C. albicans* completely lost viability within 15 minutes, gram-negative bacteria survived in relatively large numbers even after 24 hours of incubation. The composition BD2 caused rapid reduction (within 15 minutes) of viable bacteria for all species tested, including the yeast. This rapid "decontamination" of the samples is particularly desirable in the context of prolonged sample transport at ambient temperature conditions. More specifically, TB positive sputum samples will be less likely to be discarded due to putrefaction if a broad range of rapidly growing background bacteria can be quickly and effectively eliminated. This example demonstrates that the STC compositions are effective in eliminating the viability of a broad range of microorganisms with differing physical characteristics and originating from diverse environments.

Example 13: DNA from *Mycobacterium tuberculosis* can be Extracted from Human Sputum Samples Stored in STC Compositions and Frozen at −80° C. for 1 Week While the cost of freezing samples as a method of preservation is prohibitively expensive in many developing countries, it is a method often used in wealthier nations. A composition that offers not only the important benefits of ambient temperature stabilization, but is also able to integrate into molecular diagnostic workflows that incorporate freezing steps is a clear advantage. This example assesses the impact of freezing on the ability to extract DNA suitable for downstream use.

Materials
1. 1.5×10$^9$CFU/mL attenuated *Mycobacterium tuberculosis* (strain h37a; aMTB) in PBS (stored at 4° C.).
2. 2-3 mL sputum samples from Tissue Solutions (stored at −80° C.).
3. Filter-sterilized BD2 (50 mM glycine, 250 mM LiCl, 50 mM CDTA, 2% SDS; pH 10.5)
4. Sodium (meta) periodate (NPI).
5. M7H9 liquid medium (prepared from 2714 Middlebrook 7H9 broth with OADC enrichment and 40 mM sodium pyruvate).

Experimental Methods
1. Sputum was spiked as below and frozen in −80° C. in cryological vials for 1 week before extraction and culture:

| Sample Number | Sputum Volume | BD2 Volume | aMTB Volume[1] | aMTB Concentration[2] |
|---|---|---|---|---|
| 1 | 600 µL | 600 µL | 100 µL | $2.0 \times 10^7$ CFUs/100 µL |
| 2 | 600 µL | 600 µL | 100 µL | $2.0 \times 10^7$ CFUs/100 µL |

[1] From a 5 McFarland suspension
[2] Final concentration in sputum/STC mixture

2. On the day of processing, the samples were thawed and 200 µL aliquots were made in 1.5 mL screw-cap tubes.
3. They were spun at 3,500 g for 20 minutes, the supernatant discarded and the pellet was brought up in 100 µL PBS.
4. DNA was purified from samples using an abbreviated version of the method outlined in Example 1 (Extraction of DNA from aMTB-spiked BD2 Buffer-Treated Sputum using the Periodate Method; specifically, steps 8-14 were used).
5. DNA isolated from aMTB-spiked sputum was used in the *Mycobacterium* specific RD4 Taqman Real-time PCR assay as described in Example 1 (see rtPCR Conditions).

Results

TABLE 19

$C_t$ values obtained from RD4 PCR using DNA isolated from aMTB spiked human sputum samples mixed with STC composition BD2.

| Chemistry/sample | Test Condition | aMTB concentration | $C_t$ value |
|---|---|---|---|
| BD2/human sputum | 1 week frozen (−80° C.) | $2.0 \times 10^7$ CFUs (100 µL) | 21.52 |
|  |  | $1.0 \times 10^7$ CFUs (50 µL) | 22.26 |
|  |  | $2.0 \times 10^6$ CFUs (10 µL) | 26.31 |
| BD2/human sputum | 3 h RT (ambient temp) | $2.0 \times 10^7$ CFUs (100 µL) | 21.78 |
|  |  | $1.0 \times 10^7$ CFUs (50 µL) | 23.46 |
|  |  | $2.0 \times 10^6$ CFUs (10 µL) | 24.02 |

Conclusion

As can be seen in Table 19, the $C_t$ values obtained from the RD4 PCR are very similar in both frozen and non-frozen sputum samples spiked with aMTB. This is in line with results described by Holz et al. (2001) where freezing (−20° C.) did not affect sputum morphology or cell counts. Thus the STC compositions are not only ideally suited for use in areas where refrigeration is costly or inaccessible, but is also suitable for laboratory workflows where frozen storage is the norm. This example demonstrates broad utility of the STC compositions. When samples containing hardy microorganisms such as *Mycobacterium tuberculosis* are mixed with STC compositions, the microorganisms are stabilized at a variety of storage conditions and they can be recovered many days post collection. The DNA can then be recovered for further use in molecular diagnostic assays.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

Wilson M L (1996) General principles of specimen collection and transport. *Clin Inf Dis* 22: 766-777.

Parmasivan C N, Narayana A S, Prabhakar R, Rajagopal M S, Somasundaram P R, Tripathy S P (1983) Effect of storage of sputum specimens at room temperature on smear and culture results. *Tubercle* 64(2): 119-124.

Effthimiadis A, Jayaram L, Weston S, Carruthers, S, Hargreave F E (2002) Induced sputum: Time from expectoration to processing. *Eur Respir J* 19: 706-708.

Burdz T V, Wolfe J, Kabani A (2003) Evaluation of sputum decontamination methods for *Mycobacterium tuberculosis* using viable colony counts and flow cytometry. *Diagn Microbiol Infect Dis* 47: 503-509.

Holz 0, Mücke M, Zarza P, Loppow D, Jörres RA, Magnussen H (2001) Freezing of homogenized sputum samples for intermittent storage. *Clin Exp Allergy* 31: 1328-1331.

Popov T A, Petlichkovski A, Mustakov T B, DuBushe L M, Popova D N (2004) Assessment of a protocol for sputum freezing and subsequent examination. *J Allergy Clin Immunol* 113: S193.

Kelly M M, Hargreave F E, Cox G E (2003) A method to preserve sputum for delayed examination. *Eur Respir J* 22: 996-1000.

Dorman S C, Bussoli M A, Ritz S A (2010) Alcohol fixation of induced sputum samples for applications in rural communities. *Can Respir J* 17(3): 115-121.

Silverstolpe L (1948) Förbättrad metod för påvisande av tuberkelbakterier. *Nord Med* 48: 2220-2222.

Lipsky B A, Gates J, Tenover F C, Plorde J J (1984) Factors affecting clinical value of microscopy for acid-fast bacilli. *Rev Infect Dis* 6: 214-222.

Krasnow I, Wayne L G (1966) Sputum digestion. I The mortality rate of tubercle bacilli in various digestion systems. *Am J Clin Pathol* 45: 352-355.

Thornton C G, MacLellan K M, Brink T L J R, Lockwood D E, Romagnoli M, Turner J, Merz W G, Schwalbe R S, Moody M, Lue Y, Passen S (1998) Novel method for processing respiratory specimens for detection of mycobacteria by using C18-carboxypropylbetaine: Blinded study. *J Clin Microbiol* 36(7): 1996-2003.

Kent P T, Kubica G P (1985) Public Health Microbiology, a Guide for the Level III Laboratory. Centers for Disease Control, Division of Laboratory Training and Consultation. Atlanta, Ga., US Department of Health and Human Services, US Government Printing Office.

Selvam J M, Wares F, Perumal M, Gopi P G, Sudha G, Chandrasekaran V, Santha T (2007) Health-seeking behaviour of new smear-positive TB patients under a DOTS programme in Tamil Nadu, India. *Int J Tuberc Lung Dis* 11: 161-167.

Paramasivan C N, Narayana A S, Probhakar R, Rajagopal M S, Somasundaram P R, Tripathy S P (1983) Effect of storage of sputum specimens at room temperature on smear and culture results. *Tubercle* 64(2): 119-124.

Hammerschlag M R, Harding L, Macone A, Smith A L, Godlmann D A (1980) Bacteriology of sputum in cystic fibrosis: Evaluation of dithiothreitol as a mucolytic agent. *J Clin Microbiol* 11(6): 552-557.

Morris S, Bai G H, Suffys P, Portillo-Gomez L, Fairchok M, Rouse D (1995) Molecular mechanisms of multidrug resistance in clinical isolates of *Mycobacterium tuberculosis*. *J Infect Dis* 171: 954-960.

Gopinath K and Singh S (2009) Multiplex PCR assay for simultaneous detection and differentiation of *Mycobacterium tuberculosis, Mycobacterium avium* complexes and other Mycobacterial species directly from clinical specimens. *J Appl Microbiol* 107: 425-435.

Park H, Jang H, Kim C, Chung B, Chang C L, Park S K, Song S (2000) Detection and identification of mycobacteria by amplification of the internal transcribed spacer regions with genus and species-specific PCR primers. *J Clin Microbiol* 38: 4080-4085.

Telenti A, Marchesi F, Balz M, Bally F, Bottger E C, Bodmer T (1993) Rapid identification of mycobacteria to the species level by polymerase chain reaction and enzyme analysis. *J Clin Microbiol* 31: 175-178.

US Centers for Disease Control and Prevention (CDC, 2009) Updated guidelines for the use of nucleic acid amplification tests in the diagnosis of tuberculosis. *MMWR Morb Mortal Wkly Rep* 58: 7-10.

Halse T A, Edwards J, Cunningham P L, Wolfgang W J, Dumas N B, Escuyer V E, Musser K A (2010) Combined real-time PCR and rpoB gene pyrosequencing for rapid identification of *Mycobacterium tuberculosis* and determination of rifampin resistance directly in clinical specimens. J Clin Microbiol 48(4): 1182-1188.

The embodiments of the present invention for which an exclusive property or privilege is claimed are defined as follows:

1. A method for preserving viable hardy bacteria in a biological sample at ambient temperature, comprising contacting the biological sample with a stabilization composition to form a mixture, and storing the mixture at ambient temperature, wherein the stabilization composition comprises a chelating agent, a denaturing agent, an inorganic salt and has a pH between 6 and 11,
   wherein
   the hardy bacteria are pathogenic bacteria comprising one or more species of *Mycobacterium* and/or *Bacillus anthracis,*
   the denaturing agent is an anionic detergent or a non-ionic detergent,
   the inorganic salt comprises lithium chloride, lithium bromide, lithium iodide, lithium acetate, or any combination thereof,
   the chelating agent is ethylene glycol tetraacetic acid (EGTA), (2-Hydroxyethyl)ethylenediaminetriacetic acid (HEDTA), diethylene triamine pentaacetic acid (DTPA), nitrilotriacetic acid (NTA), ethylenediaminetriacetic acid (EDTA), cyclohexanediaminetetraacetic acid (CDTA), N,N-bis(carboxymethyl)glycine, citrate anhydrous, sodium citrate, calcium citrate, ammonium citrate, ammonium bicitrate, citric acid, diammonium citrate, ferric ammonium citrate, lithium citrate, or any combination thereof; and the stabilizing composition does not comprise a reducing agent, wherein storing the mixture at ambient temperature comprises storing the mixture at a temperature within the range of from 4° C. to 40° C., wherein the stabilization composition preserves, in a viable state, and hardy bacteria in the biological sample and reduces or eliminates other microbial growth in the sample.

2. The method of claim 1, wherein the one or more *Mycobacterium* is *Mycobacterium tuberculosis* and wherein the *Bacillus anthracis* is stabilized as spores.

3. The method of claim 2, wherein the *Mycobacteria* hardy bacteria are *Mycobacterium tuberculosis*.

4. The method of claim 1, wherein the biological sample is a mucoid bodily fluid.

5. The method of claim 4, wherein the mucoid biological fluid is sputum or saliva.

6. The method of claim 1, wherein the composition comprises (i) 2% SDS, 12.5 mM CDTA, 250 mM LiCl, 50 mM glycine and has pH 10.5; or (ii) 4% SDS, 50 mM CDTA, 250 mM LiCl, 140 mM LiOH and has pH 6.8.

7. The method of claim 1, wherein all or a portion of the hardy bacteria remain stable following storage at room temperature for 1 day or more, 2 days or more, 3 days or more, 4 days or more, 5 days or more, 6 days or more or 7 days or 1 month or more.

8. The method according to claim 1, wherein the stabilizing composition liquefies the biological sample.

9. The method of claim 8, wherein the denaturing agent is an anionic detergent.

10. The method of claim 9, wherein the anionic detergent is sodium dodecyl sulfate (SDS), lithium dodecyl sulphate or sodium lauroyl sulfate (SLS).

11. The method of claim 8, wherein the denaturing agent is a non-ionic detergent.

12. The method of claim 8, wherein the biological sample is a mucoid bodily fluid.

13. The method of claim 12, wherein the mucoid bodily fluid is sputum or saliva.

14. The method of claim 8, wherein the composition comprises (i) 2% SDS, 12.5 mM CDTA, 250 mM LiCl, 50 mM glycine and has pH 10.5; or (ii) 4% SDS, 50 mM CDTA, 250 mM LiCl, 140 mM LiOH and has pH 6.8.

15. The method of claim 1, wherein the denaturing agent is an anionic detergent.

16. The method of claim 15, wherein the anionic detergent is sodium dodecyl sulfate (SDS), lithium dodecyl sulphate or sodium lauroyl sulfate (SLS).

17. The method of claim 1, wherein the denaturing agent is a non-ionic detergent.

* * * * *